United States Patent
Dave et al.

(10) Patent No.: US 9,107,851 B2
(45) Date of Patent: Aug. 18, 2015

(54) SOLVENTLESS MIXING PROCESS FOR COATING PHARMACEUTICAL INGREDIENTS

(71) Applicant: New Jersey Institute of Technology, Newark, NJ (US)

(72) Inventors: Rajesh N. Dave, Princeton, NJ (US); Daniel To, North Wales, PA (US); Maxx Capece, Monclair, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 68 days.

(21) Appl. No.: 13/651,977

(22) Filed: Oct. 15, 2012

(65) Prior Publication Data
US 2014/0106059 A1    Apr. 17, 2014

(51) Int. Cl.
*A61K 35/00* (2006.01)
*A61K 9/50* (2006.01)

(52) U.S. Cl.
CPC ............. *A61K 9/5042* (2013.01); *A61K 9/5063* (2013.01); *A61K 9/5073* (2013.01); *A61K 9/5089* (2013.01); *A61K 35/00* (2013.01)

(58) Field of Classification Search
CPC ........... A61K 35/00; A61K 9/14; H05K 7/14; B05D 3/00
USPC ............ 426/654; 524/832; 65/17.3; 424/494; 427/2.14; 429/218; 252/358
See application file for complete search history.

(56) References Cited

U.S. PATENT DOCUMENTS

| | | | | |
|---|---|---|---|---|
| 5,565,284 | A | * | 10/1996 | Koga et al. ................... 429/217 |
| 5,628,945 | A |  | 5/1997 | Riman et al. |
| 5,769,917 | A | * | 6/1998 | Belko et al. ................... 65/17.3 |
| 6,740,341 | B1 |  | 5/2004 | Holt et al. |
| 7,862,848 | B2 |  | 1/2011 | Zhu et al. |
| 2002/0115785 | A1 | * | 8/2002 | Weitzel et al. ............... 524/832 |
| 2005/0228075 | A1 |  | 10/2005 | Gogps et al. |
| 2006/0210694 | A1 | * | 9/2006 | Chappell et al. ............. 426/654 |
| 2013/0071481 | A1 | * | 3/2013 | Ichikawa et al. ............. 424/494 |

FOREIGN PATENT DOCUMENTS

| | | | |
|---|---|---|---|
| WO | WO2011155451 A1 | 12/2011 | |
| WO | WO2011/155451 | * 12/2011 | ............... A61K 9/14 |
| WO | WO2013144655 A1 | 10/2013 | |

OTHER PUBLICATIONS

Cerea M., et al., "A Novel Powder Coating Process for Attaining Taste Masking and Moisture Protective Films Applied to Tablets," International Journal of Pharaceutics, Elsevier BV, NL, vol. 279, No. 1-2, Jul. 26, 2004, pp. 127-139.

(Continued)

*Primary Examiner* — Dah-Wei D Yuan
*Assistant Examiner* — Andrew Bowman
(74) *Attorney, Agent, or Firm* — Mendelsohn, Drucker & Dunleavy, P.C.

(57) ABSTRACT

The present invention is a solventless method of producing polymer coated active pharmaceutical ingredient that is taste-masked and may be released in relatively short time. It employs high energy vibrations or acoustic mixing of API particles, water soluble coating material particles and hydrophobic polymer particles, with or without use of other pharmaceutically relevant powders as media. Additionally the method is capable of producing individually coated drug particles without agglomeration or the long drying times associated with solvent based coating methods.

37 Claims, 27 Drawing Sheets

(56) References Cited

OTHER PUBLICATIONS

International Search Report and Written Opinion; Mailed Dec. 2, 2013 for corresponding PCT Application No. PCT/US2013/064058.

Obara, S; Maruyama, N; Nishiyama, Y; Kokubo, H., "Dry coating: an innovative enteric coating method using a cellulose derivative," European Journal of Pharmaceutics and Biopharmaceutics, vol. 47, 1999, pp. 51-59.

Kim, J; Satoh, M; Iwasaki, T., "Mechanical-dry coating of wax onto copper powder by ball milling," Materials Science and Engineering A, vol. 342, 2003, pp. 258-263.

Wang, P; Zhu, Linjie; Teng, S; Zhang, Q; Young, MW; Gogos, C., "A novel process for simultaneous milling and coating of particulates," Powder Technology, vol. 193, 2009, 65-68.

Zhang, Q; Wang, P; Qian, Z; Zhu, Linjie; Gogos, C., "Simultaneous Milling and Coating of Inorganic Particulates with Polymeric Coating Materials Using a Fluid Energy Mill," Polymer Engineering and Science, vol. 50, 2010, pp. 2366-2374.

Yang, J., Sliva, A., Banerjee, A., Davé, R.N., Pfeffer, R., Dry particle coating for improving the flowability of cohesive powders, (2005) Powder Technology, Special Issue in Memory of Prof. Molerus, 158 1-3, pp. 21-33.

Yuhua Chen, Jun Yang, Rajesh N. Davéand Robert Pfeffer, "Fluidization of Coated Group C Powders," AIChE Journal, vol. 54, Issue 1, pp. 104-121, Jan. 2008.

Yuhua Chen, Miguel A.S. Quintanilla, Jun Yang, Jose M. Valverde and Rajesh N. Davé, "Pull-off Force of Coated Fine Powders under Small Consolidation," Physical Review E, 79, pp. 041305, Jun. 2009.

Yuhua Chen, Laila Jallo, Miguel A. S. Quintanilla and Rajesh Davé, "Characterization of Particle and Bulk Level Cohesion Reduction of Surface Modified Fine Aluminum Powders", Colloids and Surfaces A: Physicochemical and Engineering Aspects, vol. 361, pp. 66-80, Apr. 2010.

Laila J. Jallo, Yuhua Chen, James Bowen, Frank Etzler, and Rajesh Davé, Prediction of Inter-particle Adhesion Force from Surface Energy and Surface Roughness, Journal of Adhesion Science and Technology, vol. 25 (2011) 367-384.

Dave K. Balachandran, Laila J. Jallo, Rajesh N. Davé, Stephen P. Beaudoin, "Adhesion of Dry Nano-Coated Particles to Stainless Steel: A Physical Interpretation", Powder Technology, 226, pp. 1-9, 2012.

\* cited by examiner

Figure 25B without media discrete

SOLVENTLESS MIXING PROCESS FOR COATING PHARMACEUTICAL INGREDIENTS

BACKGROUND OF THE INVENTION

1. Field of the Invention

The present invention relates to coating active pharmaceutical ingredients for controlled release or applications associated with controlled release such as taste masking. In particular, it is directed to a particulate pharmaceutical formulation coated with both a water soluble or swellable coating material and a substantially water insoluble polymer and a process of producing the same.

2. Description of the Related Technology

Compliance with medication requirements is a significant challenge for patients who have difficulties swallowing, such as young children, the very elderly and patients with dysphagia. The pharmaceutical industry has developed a number of drug delivery protocols to address this challenge, including rapid in-mouth disintegrating tablets, tablets which disintegrate in liquid prior to ingestion, liquids and syrups, gums and even transdermal patches. Unfortunately, each of these methods has its own problems. For example, transdermal patches can be inconvenient or uncomfortable and can be quite expensive to produce. The flux of drug through the skin can also create complex dosing issues.

Masking the undesirable taste of an active pharmaceutical ingredient (API) will make it pleasant to chew and swallow, therefore easier for patients to comply with their medication requirements. Microencapsulation is a taste masking process in which a particle is encased by coating, and therefore may be capable of masking the taste of API. Microencapsulation has been used for many commercial applications such as in pharmaceuticals, cosmetics, agricultural products, and copier toners.

Many microencapsulation methods require solvents, such as wet methods and spray drying methods. The solvents, especially organic solvents, may result in environmental pollution and hazardous conditions during the manufacturing process. Organic solvents also add extra cost in addition to increasing energy costs and requiring relatively long processing times. Thus, it is desirable to develop taste masking methods that do not use solvents.

Two types of methods have been developed for this purpose, methods using plasticizers and methods using mechanical energy to apply the coating. The methods employing plasticizers are limited to coarse particles/granules/pellets/tablets with a size greater than 500 microns. Mechanical coating methods may break the core particles into undesirably small particles and are typically limited to the application to coating of robust particles with relatively thin coating layers of only about 1-5 microns in thickness. The advantages of mechanical coating are that typically no plasticizer and no thermal treatment are required to prepare the coating.

Obara et al. discloses a dry coating method using polymer powders (Obara, S; Maruyama, N; Nishiyama, Y; Kokubo, H., "Dry coating: an innovative enteric coating method using a cellulose derivative," *European Journal of Pharmaceutics and Biopharmaceutics*, Vol. 47, 1999, pages 51-59). This method involves direct feeding of polymer powder and simultaneous spraying of plasticizing agent, with neither an organic solvent nor water, using a centrifugal granulator, fluidized bed, or tablet-coating machine. The method requires a higher loading of coating to achieve gastric resistance compared with a conventional coating, but the processing time was dramatically reduced.

Kim et al. discloses a mechanical dry coating process (Kim, J; Satoh, M; Iwasaki, T., "Mechanical-dry coating of wax onto copper powder by ball milling," *Materials Science and Engineering A*, Vol. 342, 2003, pages 258-263). The process produces an oxidation resistant film of polymer wax on spherical copper particles (median diameter of 69.1 µm) using a conventional ball milling process. The polymer wax functions as a sealant material for filling the cavities of the hard wax, which can effectively stabilize the coating and enhance the degree of coverage.

Wang et al. discloses a coating process wherein ascorbic acid particulates are milled and coated simultaneously with fine wax particles using fluid energy milling (Wang, P; Zhu, Linjie; Teng, S; Zhang, Q; Young, M W; Gogos, C., "A novel process for simultaneous milling and coating of particulates," *Powder Technology*, Vol. 193, 2009, 65-68). During the milling process, ascorbic acid particulates collide with each other, wax powder particles and the wall to produce fine particles within a discrete polymer coating. This novel process has several advantages such as elimination of solvent usage, reduction of agglomeration, and vastly improved production efficiency. The core particles are also typically ground to fine particles of about 10 microns in diameter.

Zhang et al. discloses a fluid energy-based method and apparatus for simultaneously milling and coating coarse particles (Zhang, Q; Wang, P; Qian, Z; Zhu, Linjie; Gogos, C., "Simultaneous Milling and Coating of Inorganic Particulates with Polymeric Coating Materials Using a Fluid Energy Mill," *Polymer Engineering and Science*, Vol. 50, 2010, pages 2366-2374). The coating materials include three micron-sized particles—carnauba wax, polyethylene (PE), and polytetrafluoroethylene (PTFE) particles, and one type of nanoparticle. The polymeric coating, which functions as a lubricant and cushioning layer, absorbs part of the kinetic energy and produces coated particles with larger particle sizes. Again the core particles are typically ground to fine powders in this process.

U.S. Pat. No. 7,862,848 discloses a method and apparatus for dry coating solid dosage forms. The method includes the steps of placing solid dosage forms in a rotatable, electrically grounded housing, and spraying a film-forming polymer powder composition into the housing during rotation thereof to form a polymer coating on the solid dosage forms. The polymer powder composition is sprayed using an electrostatic spray gun. Curing of the polymer coating on the solid dosage form is also required.

U.S. Pat. No. 5,628,945 discloses a method of dry coating core particles with a controlled distribution of substances in a solid state. Ball milling and mechanofusion are used to produce granulated ceramic particles in a metal-organic matrix. Heat treatment and multiple processing steps are required to achieve granules of microencapsulated particles. The method produces a structured coating and a controlled level of subdivision on the core particles. The method can also be used to agglomerate the microcapsules into granules.

There remains a need for improved solventless processes for coating API's. More specifically, solventless processes for coating API's having acceptable processing times are desirable. In addition, a process capable of coating fine particles to provide a product with improved mouth feel and without attrition/breakage is also desirable. Such coatings should also provide release of the API in a relatively short time once the API is ingested or a more gradual release of the API for extended release formulation.

SUMMARY OF THE INVENTION

In a first aspect, the present invention is directed to a process for preparing a particulate pharmaceutical formulation from core particles comprising an active pharmaceutical ingredient. The core particles are mixed with a water soluble and/or water swellable coating material and substantially water insoluble polymer particles, to produce a discrete coating on the particulate pharmaceutical formulation comprising coated core particles. Subsequently, the coated particulate pharmaceutical formulation is subjected to mechanical stress to deform the coating into a continuous film. The coating results in a significant delay or reduction in API release for at least the first minute of release in the mouth but allows at least 90% of the amount of API that would have been released absent the coating, to be released from the coated particulate pharmaceutical formulation, both as measured at 30 minutes in a standard USP dissolution test.

The present invention provides a solventless method of producing polymer coated API such that the release of the API in the first one or two minutes in the mouth is controlled, yet substantially all of the API is released in relatively short time. The process may employ high energy vibrations or acoustic mixing of API particles, soluble and/or swellable coating material particles and substantially water insoluble polymer particles, with or without use of other media. The method is capable of producing individually coated drug particles without agglomeration and avoiding or minimizing breakage and the long drying times associated with solvent based coating methods.

Another aspect of the present invention is directed to a taste-masked, coated particulate pharmaceutical formulation comprising a core that comprises an API, and a coating that results in a significant delay or reduction in API release for at least the first minute of release in the mouth but allows at least 90% of the amount of API that would have been released absent the coating, to be released from the coated particulate pharmaceutical formulation, both as measured at 30 minutes in a standard USP dissolution test.

BRIEF DESCRIPTION OF THE DRAWINGS

FIG. 25B is an SEM image of ascorbic acid particles with a discrete polymer layer at high magnification.

DETAILED DESCRIPTION OF THE PREFERRED EMBODIMENT(S)

Figure 1:
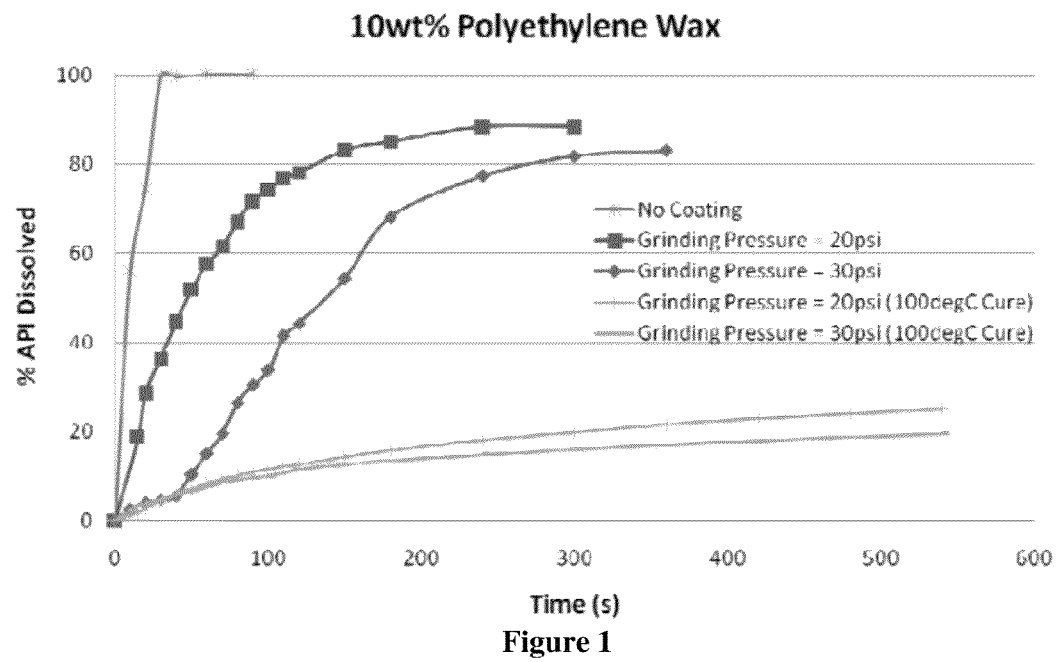
FIG. 1 shows dissolution profiles of ascorbic acid coated with polyethylene (PE) wax using a fluid energy mill (FEM).
Figure 2A:
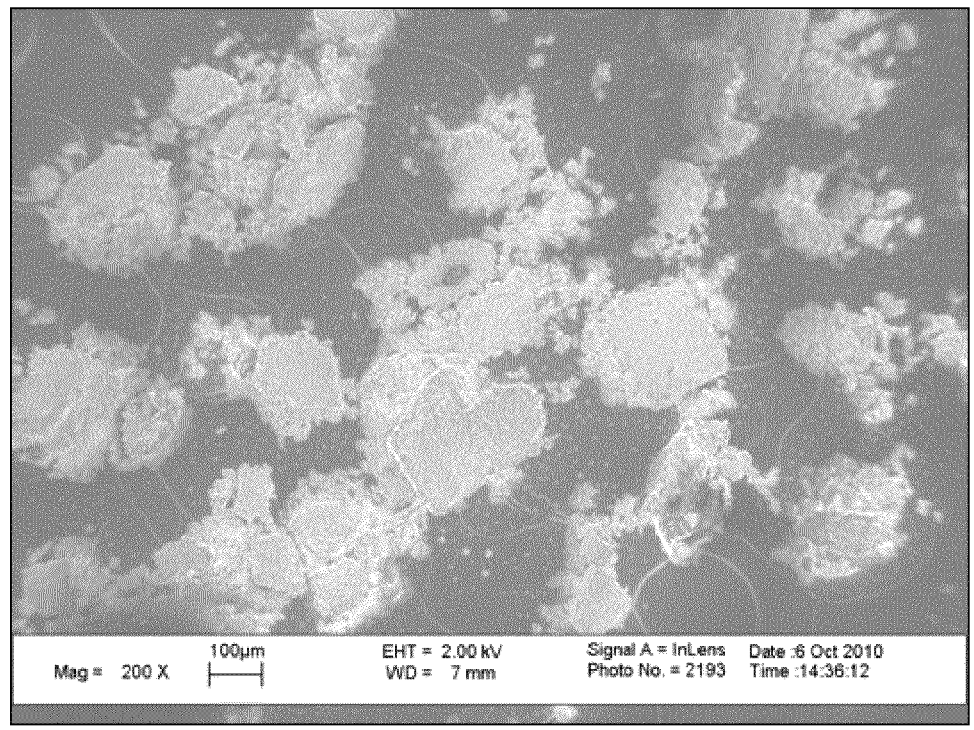
FIG. 2A is a scanning electron microscope (SEM) image of ascorbic acid coated with 20 wt % polyethylene (PE) wax at low magnification.
Figure 2B:
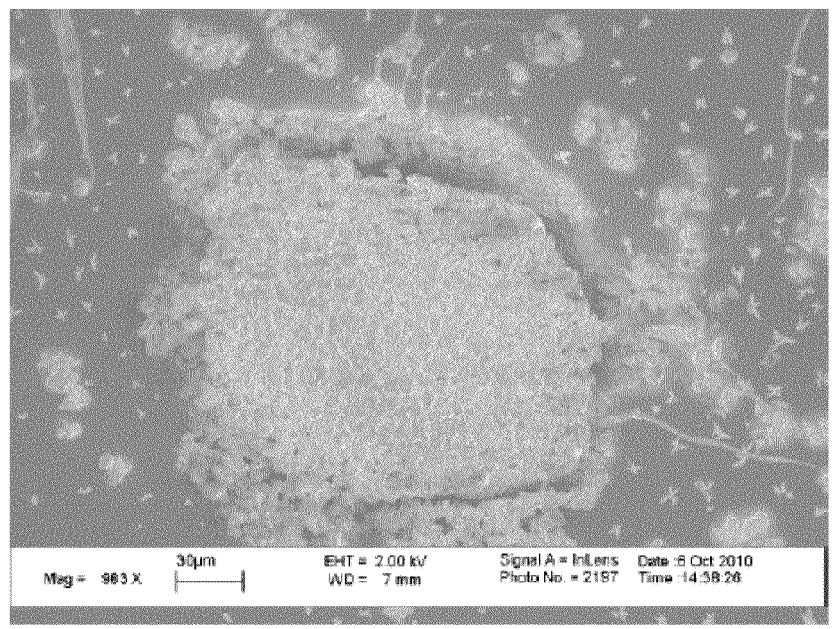
FIG. 2B is an SEM image of ascorbic acid coated with 20 wt % PE wax at high magnification.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation.

Although certain methods are described with reference to steps that are presented herein in a certain order, in many instances, these steps may be performed in any order as may be appreciated by one skilled in the art; the novel method is therefore not limited to the particular arrangement of steps disclosed herein. Furthermore, each of the numerous embodiments of the materials and methods disclosed herein have been described in a shorthand manner and thus it is to be understood that each embodiment, selection, range or other feature of the materials and/or methods described herein can be combined with any one or more other embodiments, selections, ranges or other features described in the present application.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

The present invention relates to a solventless coating process for preparing a taste masked pharmaceutical formulation. The solventless coating process of the present invention can also be used without a liquid plasticizer. The solventless coating process starts from core particles that comprise an API. The coating materials include a soluble coating material and a substantially water insoluble polymer.

The present invention is also a mechanical, dry process. API's with particle sizes of from 30 μm to 2 mm may be coated. The method is especially effective in coating API particles at the lower end of the size range (i.e. less than 100 μm). Coating can be used for taste masking, controlled release, film coating of all types of hosts or any combination thereof. Coating is more attractive for water-soluble APIs because granulating them (which is another standard approach) can be difficult. Coating of fine or difficult to fluidize particles containing APIs (i.e. particles having a diameter of less than 100 microns) can also be a problem using prior processes.

The present invention uses a combination of a water soluble and/or water swellable coating material and a substantially water insoluble coating material, at least one of which is deformable so that a film can be created by the coating process. The present invention uses this combination of coating materials to achieve a controlled release formulation.

The process of the invention may be solventless and preferably does not require use of a plasticizer. In one embodiment of the process of the invention, a media, such as a bi-modal mixture of host particles or a polydisperse mixture of host particles, is employed to achieve coating of finer hosts and also avoid or minimize attrition of large particles. Other media of non-host material such as sugars or glass beads may also be employed. The same coating process is also suitable for non-pharmaceutical materials but is exemplified herein using API's.

In a first step of the process of the present invention, the API core particles are mixed with a combination of water soluble and/or swellable coating material particles, and water insoluble polymer particles, to produce coated API core particles wherein the water soluble and/or swellable particles are imbedded within a water insoluble, deformable continuous polymer layer. The coated API core particles are then subjected to mechanical stress, elevated temperature or a combination thereof in order to deform the coating into a continuous film. The API in the coated API core particles does not release immediately in the mouth and thus the particles can be taste masked in this manner, yet the API is released in a relatively short time from the coated pharmaceutical formulation.

The API core particles may comprise an active pharmaceutical ingredient that has undesirable taste or which causes numbness. Any type of API may be coated by the process of the present invention for the purpose of altering the dissolution rate. API's having an undesirable taste or which cause numbness can also be taste masked using the process of the present invention. Exemplary API's which may be coated in the process of the present invention include, but are not limited to, ascorbic acid, ibuprofen, metformin, Acetaminophen, Cetirizine, Indeloxazine, Ondansetron, Artemether, Niflumic acid, Diclofenac, medications for erectile dysfunction and other non-steroidal anti-inflammatory drugs.

The core particles may have a volume averaged median particle size in a range of from 10 µm to 2000 µm, in a range of from 10 µm to 1000 µm, in a range of from 40 µm to 500 µm, in a range of from 30 µm to 400 µm, or in a range of from 40 µm to 300 µm. In some embodiments, the API core particles may have a volume averaged median particle size close to the lower end of the range, i.e. from 30 µm to 100 µm.

The API core particles may comprise two or more active pharmaceutical ingredients, either in separate particles or in the same particle. This may offer advantages for combination therapies where two drugs may be formulated into the same pharmaceutical formulation. The API core particles may be formed from an API or may comprise an API formulated with other pharmaceutically acceptable ingredients.

In some embodiments, combinations of API core particles having significantly different particle sizes may be employed. For example, two sizes of API core particles may be employed wherein one size of API core particles is 1-100 times, or 3-10 times the size of the other API core particles. For example, one size of API core particles may have a volume averaged median particle size in a range of from 250-1000 µm, more preferably 300 µm to 500 µm. The other size of API core particles may have a volume averaged median particle size in a range of from 20 µm to 100 µm.

In some embodiments, the use of API core particles of dissimilar sizes can provide polymer coatings on both sizes of API core particles with better taste masking properties than use of only API core particles having a similar size. The use of significantly different particle sizes during mixing has been shown to provide a continuous film coating on the particles.

The water soluble and/or swellable material is in particle form, with a median particle size in a range of from 0.5 µm to 20 µm, or in a range of from 1 µm to 10 µm. The water swellable material is a material that swells upon absorption of water and may be selected from typical disintegrants used in the pharmaceutical industry as additives for blends made for tableting. Exemplary water swellable materials include crospovidone, croscarmellose and sodium starch glycolate. Such materials, if not soluble in water, must swell upon absorption of water such that their diameter can increase to 120-600% of their original diameter prior to water exposure, more preferably, 200-600%. Materials that swell even more could also be used but such a high degree of swelling is not necessary for success.

The water soluble material has a solubility of at least 50 mg/ml in water at neutral pH and 20° C. The water soluble material should be readily soluble in water and have an intrinsic dissolution rate of 3-60 µg/m$^2$s. Water soluble materials having higher intrinsic dissolution rates of 60-300 µg/m$^2$s may also be used but should first be coated with a hydrophobic silica layer in an amount of 100-300% surface coverage, as discussed in greater detail below. Examples of water soluble materials include micronizable materials such as sugars such as sucrose, polyols such as mannitol and sorbitol, polyvinylpyrrolidone, ethylcellulose, hydroxypropylmethylcellulose (HPMC), hydroxypropylcellulose (HPC), lactose, and poly-(ethylene oxide) (PEO), polymethacrylates (Eudragit brand polymers), and combinations thereof. Hydrophilic polymers are a particularly useful class of materials that may be used.

The amount of water soluble and/or water swellable material employed in the mixing step is in a range of from 0.1 wt. % to 25 wt. %, or from 0.5 wt. % to 13 wt. % of the total weight of the API core particles and coating materials.

Particles coated with the water soluble and/or water swellable material may be optionally dry coated with hydrophobic silica to a SAC from 100% to 400% to slow the dissolution rate of the API. This option is especially beneficial for coating materials that dissolve and/or swell too quickly to mask the API's taste. Dry coating with hydrophobic silica may produce a poorly wetting but still soluble particle.

The silica particles used for dry coating include hydrophobic silica or hydrophobically treated silica. Examples include Aerosil R972 silica (Degussa), CAB-O-SIL EH-5 silica (Cabot), OX-50 silica (Degussa), COSM055 (Catalyst & Chemical Ind. Co. Ltd (Japan)), P-500 hydrophilic silica (Catalyst & Chemical Ind. Co. Ltd (Japan)) and TS5 silica (Cabot). In some embodiments, more than one type of silica may be used in combination. For example, TS5 and Aerosil R972 may be used together to coat the API core particles.

Dry coating with silica may be accomplished by any suitable device known to a skilled person. Suitable devices include, but not limited to, Comil (U3 Quadro Comil of Quadro Pennsylvania, U.S.), LabRAM (Resodyne Minnesota, U.S.), Magnetically Assisted Impact Coater (MAIC, Aveka Minnesota, U.S.) and Fluid Energy Mill (FEM, Qualification Micronizer of Sturtevant Massachusetts U.S.) The FEM is able to simultaneously mill and dry coat the particles to achieve particle sizes that are equal to or less than 50% of the initial particle size if smaller particles are desired. Dry coating of the particles can be accomplished in a relatively short time using such equipment, for example, 100 grams of coated API core particles may be dry coated in 5 to 10 minutes using a LabRAM.

The water-insoluble polymer is also in particle form, with a median particle size in a range of from 1 µm to 20 µm, from 5 µm to 12 µm or from 5-6 µm. The water insoluble polymer is deformable under mechanical stress, elevated temperature or a combination thereof and thus is selected to have a Young's modulus of not greater than 420 MPa, or not greater than 200 MPa, or not greater than 100 MPa, as measured at 20° C. Alternatively, the deformability should be equivalent to a Young's modulus of not greater than 420 MPa or not greater than 200 MPa, or not greater than 100 MPa, as measured at 20° C. when measured at elevated or reduced temperatures actually used for processing. Thus, it is contemplated, for example, that elevated processing temperatures could be employed to soften the water insoluble polymer for deformation or that a combination of softening at elevated temperature and mechanical stress can be employed.

The water insoluble polymer may be selected from easily deformable micronized polymers. The water insoluble polymer may be selected from the group consisting of polyethylene, polypropylene, polytetrafluoroethylene, carnauba wax, castor wax, polyamide wax, and combinations thereof.

The water insoluble layer should allow a diffusivity of the API in the range of $0-20 \times 10^{-12}$ m$^2$/s or more preferable $5-15 \times 10^{-12}$ m$^2$/s. The coatings result in a significant delay or reduction in API release for the first minute of release or more preferably, the first two minutes of release in a dissolution test indicative of taste-release in the mouth. The coatings also permit at least 90% of the release of the uncoated API core particles at 30 minutes in a standard USP dissolution test indicative of dissolution in the GI tract. Specifically, in the first 60 seconds, the release from the test sample consisting of coated particles is nearly arrested by the coating, with less than 0.1% of drug dissolving in a dissolution test indicative of taste-release in the mouth, more preferably, less than 0.01% of drug dissolving in a dissolution test indicative of taste-release in the mouth. Also, in some embodiments less than about 1% of drug dissolves in a dissolution test indicative of taste-release in the mouth at 120 seconds, more preferably less than 0.5%, as compared with the release from a test-sample of uncoated drug particles of comparable size.

Successful taste-masking may be achieved through significantly delayed or nearly arrested release, it should not be detrimental to drug release in the GI tract. Therefore, the coating is such that it may not significantly impact the release profiles beyond first 5 minutes such that the amount of drug released is at least 90% of what would be released from a test sample of uncoated drug particles of comparable size in a USP dissolution test indicative of dissolution in the GI tract, more preferably, at least 95%, and even more preferably, at least 99% of what would be released from a test sample of uncoated drug particles of comparable size in a USP dissolution test indicative of dissolution in the GI tract.

The number of water insoluble polymer particles must be much larger than the number of water soluble and/or swellable particles; specifically, not counting silica as an additive, the number of water insoluble particles may be 10-1000 times the number of particles of all other coating additives or more preferably in the range of 20-100 times the number of particles of all of the other coating additives. In some embodiments, the particle number ratio between the water soluble and/or swellable particles and the water insoluble polymer particles of the mixing step is in a range of from 1:10 to 1:100, or in a range of from 1:20 to 1:80. The amount of water insoluble polymer particles employed in the mixing step is in a range of from 0 wt. % to 50 wt. %, 10 wt. % to 50 wt. % or from 5 wt. % to 25 wt. % of the total weight of the core particles and coating.

The particle number ratio between the API core particles and the particles used to coat the API core particles used in the mixing step may be adjusted based on the sizes of the particles. Generally speaking, a surface coverage of the API core particles with the coating particles of at least 90-100%, more preferably 100-200%, should be achieved. The theoretical surface coverage of the API core particles may be calculated based on the particle sizes, assuming that the particles are spherical and uniform in size. To achieve a theoretical surface coverage of 100% of the API core particles, the amount of coating particles needed may be calculated. A skilled person may adjust the calculation when the particles have different shapes or are non-uniform. In some embodiments, excess coating particles sufficient to provide a theoretical surface coverage of from 100% to 400% may be used, up to 1000% surface coverage may still be used under certain circumstances. The theoretical surface coverage is calculated as shown in Example 22 below.

The median particle sizes of water soluble and/or water swellable coating particles and water insoluble polymer particles may be selected to be within a factor of six of each other, wherein the water soluble and/or water swellable coating material particle size is preferably smaller. In certain embodiments, the water soluble and/or swellable coating material particles are larger than the water insoluble polymer particles. The size ratio of water insoluble polymer particles to the water soluble and/or water swellable coating material particles may be in the range of from 1:1.5 to 1:3. This may prevent the larger particles in the coating from protruding out of the coating. When the water soluble and/or swellable particles protrude out of the coating, poor taste masking or controlled release may be produced because the water soluble material may dissolve too quickly. On the other hand, if the water soluble and/or swellable particles are too small relative to the water insoluble polymers, the particles may not be close enough to the surface of the polymer coating, and therefore would not be able to quickly dissolve and impact the API release from the coated API core particles.

In some embodiments, both the water soluble and/or swellable materials and the substantially water insoluble polymers are deformable polymers. The deformability of at least one of the materials/polymers is important for the solventless coating of the present invention, as the material/polymer is deformed into a continuous coating by mechanical stress. In general, the deformable materials have a glass transition temperature Tg that is lower than the melting temperature. Thermoplastic polymers become rigid below their Tg, and they become soft above their Tg. Deformable polymers may be rubbery and capable of elastic or plastic deformation without fracture.

In some embodiments, the coating ingredients are pre-blended to ensure more uniform contact between the API core particles and the coating particles. Preblending is employed to produce a thorough mixture of the coating particles, i.e. water soluble and/or swellable particles and water insoluble polymer particles, generally without attrition of the particles. For example, preblending may be achieved using a LabRAM acoustic mixer at 100 G's for 1 minute, or a rolling drum rotated at 60 RPM for 1 hour.

The core particles are then mixed with the pre-blended coating particles or the coating particles can be added batch-wise or stepwise to the core particles. Mechanical stress is then applied to the coated particles by, for example, use of a more vigorous mixing step. The mixing of the ingredients in the mixing step is sufficient disperse and discretely coat the coating material onto the API particles and to subsequently deform the discrete coating on the API core particles. The collisions facilitate attachment of unattached coating particles to the surface of API core particles. Continued collisions deform the coating particles, which will form a substantially continuous coating on the surface of API core particles.

The mixing step to apply mechanical stress may be carried out for a period of from about 1 to about 40 minutes, depending on the characteristics of the coating materials, the size of the core particles and the loading. In some cases, especially involving fine core particles, a period of up to 4 hours may be used. A skilled person may determine an appropriate length for the mixing step by monitoring the size of the dry coated API particles using SEM images of samples taken at various times during the process. In some embodiments, the coating particles may be added in a stepwise fashion to the API core particles while the ingredients are being mixed. In one embodiment, the coating particles are added in three equal batches at equal intervals, instead of adding all of the coating particles to the API core particles at once. Step-wise addition of coating materials makes it possible to deform each coating layer individually rather than deforming just the outer layer.

In one embodiment, the mixing is carried out by high energy vibration. Vibration can be described by vibration intensity number where the intensity number is the acceleration of the mixing vessel divided by 9.81 m/s$^2$. Intensity numbers between 10-100 are suitable for the present invention. Coarse particles require lower intensity numbers while use of intensity numbers that are too large will cause the API to break. Finer particles require high intensity numbers of up to 100. Vibration along with particle size/density will determine the collision energy which when high enough will deform the polymers. Collision energy may be increased by adding dense media such as glass, zirconia, or steel beads or coarse materials such as sucrose. This is especially important in the coating of API's with particle sizes of less than 100 μm. For example, the ingredients may be placed in a mixing chamber, which is then shaken. The shaking causes the particles to collide at high velocity, which deforms the coating particles on the surface of API core particles to spread over the surface, thereby forming a substantially continuous coating. Devices capable of providing high energy vibration may be used in the present invention. By varying acceleration of the mixing vessel, one may achieve the desired intensity number.

In another embodiment, mixing is carried out by acoustic mixing using low frequency, high-intensity acoustic energy transferred to the mixing chamber by propagation of acoustic pressure waves into the mixing chamber. Vibration intensity numbers in the range of 10-100 are suitable with a frequency of about 60 Hz. Acoustic mixing has the advantage of no bulk flow and mixing occurs on a micro scale throughout the mixing volume. In a typical acoustic mixing device, an oscillating mechanical driver creates motion in a mechanical system comprised of engineered plates, eccentric weights and springs. This energy is then acoustically transferred to the ingredients of the mixing step in the mixing chamber. The system may be operated at resonance.

Exemplary devices for mixing include the ResonantAcoustic® mixer, the Sonic Mixer 2L or 20L, Design Integrated Technology, Inc. and the Uni-cyclone mixer; UM 113S, or larger, UM 125; manufactured by Japan Unix Company, Tokyo. For example, in a LabRAM, the mixing step provides a highly efficient way of transferring mechanical energy through acoustic pressure waves directly to the ingredients in the mixing step. The resonance is achieved by matching the operational parameters of the mixer with the properties and characteristics of the materials to be mixed. In general, any device that allows sufficient number of collisions with the appropriate intensity so that polymer deformation can take place without significant attrition of the API or host to be coated, may be used.

The device, operating conditions, processing time, and the polydispersity of the APIs to be coated can be selected by those skilled in the art such that; (a) the coating is uniform and deformed sufficiently, and (b) the process does not lead to significant attrition of the core particles. In a selected process, the water insoluble polymer should be dispersed over the API surface and subsequently mechanically deformed by, for example, tumbling, vibrating, or impaction in a suitable mixer or mill providing sufficient stress due to impactions in order to result in polymer deformation. Stress may result from mechanical interactions of the particles themselves, impaction media, the vessel wall and/or other parts of the mixer such as a blade or impeller. Suitable equipment may cause impactions by particles, media, or vessel geometry with relative velocities of about 0.01-10 m/s, or about 1-5 m/s. Such velocities of impact may not be easily measured, but can be estimated by computer simulation.

Alternately, the effect of processing can be quantified via the performance of the coated product in various other manners. The mixing intensity should be high enough so that the polymer will deform, but is not excessive so as to break or attrite the host particles or the coating layer that is already deformed and well-spread. Attrition can be determined by the presence of, or and increase of fines as measured in a particle size analyzer or identified by an increase in release of the coated API at prolonged processing times as compared to an optimum processing time. More specifically, the average size of the coated pharmaceutical powders is expected to be about the same as or larger than the original uncoated powders, e.g. the average particle size of the coated particles after process is typically not less than 90% of the original particle size; and more preferably, not less than 95% of the original particle size.

While size reduction indicates a process that may not be working well, it does not by itself ensure that the insoluble coating polymer is sufficiently deformed and well spread or that the deformed layer is not damaged due to excessive processing. The test of well-coated material due to a selected process or equipment is the ability to achieve the desired dissolution characteristics of nearly arrested dissolution initially while achieving nearly comparable dissolution to that of uncoated powder in 30 minutes. The quality of the coating imparted by the processing device may also be evaluated in other ways, such as those exemplified in Examples 24-25 below. First as illustrated in Example 24, the use of Rodos/Helos in particle size determination can indicate if the coating is well-deformed. When insoluble polymer is only discretely or loosely attached, such measurements show the presence of fines due to detachment of coated particles caused by a dispersion force exerted by the Rodos device. On the other hand, if the coating is well-deformed by the process, a significant presence of fines is not found in Rodos/Helos particle size measurements. The coated particles can also be analyzed to measure their effective surface area as shown in Example 25. Coatings prepared using insufficient intensity and/or insufficient processing time are expected to be discrete and would exhibit higher surface area than the well-deformed coatings indicating proper intensity and/or processing time. Further, if the processing time is too high, the measured surface area is expected to increase from an optimal level, suggesting attrition and/or damage of coating layer.

In some embodiments, the ingredients of the mixing step also comprise media particles to increase the number of collisions or the intensity of the collisions. The media particles may be selected from the group consisting of inorganic particles, glass beads, ceramic beads, metal beads such as stainless steel beads, salts, sugars, agate, and combinations thereof. In general, any material with density equal to or higher than the API density may be used as media. The sizes and types of medial are typically selected to avoid excessive attrition and to sufficiently deform the polymer. Any particle with a density of at least about 1.6 g/ml may be employed.

In some embodiments, the presence of media particles improves the formation of a substantially continuous polymer coating on the API core particles which may lead to better taste masking. The media particles preferably have a significantly different median particle size than the API core particles, with a typical ratio of median particle sizes being from 3:1 to 25:1, preferably from 3:1 to 10:1. The media particles or the API core particles may be selected to be the larger of the particles in different embodiments of the invention. The ratio between the number of API core particles and the number of media particles in the ingredients of the mixing step may be in a range of from 1:30 to 1:300, more preferably in a range of from 1:50 to 1:200. After the mixing of the ingredients, the media particles may be separated from the coated API core particles by sieving based on their difference in particle size. Use of different sizes of media particles and API core particles makes the separation efficient and simple. A nano-coating, applied via dry coating of nano-silica or a substantially equivalent material in a post-processing step facilitates this separation.

As an alternative to the use of media particles, two different sizes of API core particles may be employed in the process. For example, a combination of API core particles having a volume averaged median particle size in the range from 300 μm to 500 μm and API core particles with a volume averaged median particle size in the range from 30 μm to 100 μm may be employed. Both sizes of the API core particles may comprise the same API. The coated particles can be subsequently separated by, for example, sieving, based on their differences in size. In yet another embodiment, a polydispersed size distribution of API particles containing particles of in a range of 30-500 μm may be used.

Optionally, in some embodiments, the method of the present invention may employ a curing step using thermal treatment. The curing step is carried out at an elevated temperature. The curing temperature Tc is dependent on the glass transition temperature Tg or softening temperature Ts of the polymer. Generally, Tc is 5-40° C. higher, preferably 10-30° C. higher, more preferably 10-20° C. higher than the Tg or Ts. The curing time typically varies from half to an hour depending on the difference between Tc and Tg, with bigger differences demanding shorter curing time. In one embodiment, curing may be carried out in a heated air furnace while the coated API particles are intermittently agitated.

Certain types of coated API core particles may suffer from adhesion and caking during storage. To prevent this, the present invention may comprise a further step of dry coating the coated API core particles with silica, which may also aid in dispersion in the mouth. The silica may be the same silicas as described above. In one embodiment, the coated API core particles are mixed with a sufficient amount of silica particles to provide at least 100% surface coverage, e.g. 1% by weight of silica particles such as Aerosil R972 fumed silica to improve the flowability of the coated API core particle. An amount of silica in a range of from 0.1 to 2 wt %; or an amount sufficient to provide a surface area coverage from about 20 to about 100% may be used. The silica coating may be applied using a LabRAM at 50G's for 30 seconds or by simply blending the coated API core particles with the silica particles.

The coated API core particles have the taste of the API masked to allow easy swallowing or even chewing by patients. The API is still released from the coated API core particles in relatively short time. A USP Dissolution Test may be used to assess the release of API from the coated API core particles. The dissolution test employs a media of 7.2 pH phosphate buffer solution with 0.4 g/L sodium dodecyl sulfate (SDS, used to ensure wetting of the powders) at 37° C. and is carried out in USP Apparatus II (paddles) rotating at 50 RPM. The percentage of active pharmaceutical ingredient that is dissolved is measured over time. The coated API core particles can release the API in 30 minutes or less as measured in the USP Dissolution test, or in 20 minutes or less as measured in the USP dissolution test.

The process of the present invention is a solventless method for producing a substantially continuous polymer coating on the surface of API core particles. The coated API core particles are well flowing and can be rendered substantially or completely tasteless without significantly affecting the bioavailability of the active ingredient. The coated API core particles do not have suffer from significant agglomeration or long drying times that are typically associated with solvent based coating methods. Furthermore, this invention offers a substantial reduction in processing time and minimized attrition of the API core particles, without significantly impacting the powder flow properties, taste masking ability or bioavailability. When flow properties are not sufficient, application of the nano-silica coating as described above can be employed to further improve the flow properties.

The invention will now be further illustrated by the following non-limiting examples.

EXAMPLES

Example 1

A deformable polymer, polyethylene (PE) wax having a particle size of 5.5 μm, was used to coat ascorbic acid. Unless otherwise specified, this same PE wax was used in the other examples given below. The polyethylene wax had a Young's Modulus of 200 MPa and was blended with ascorbic acid at a loading of 10 wt. %. The powder was processed using a fluid energy mill (FEM) at grinding pressures of 20 psi and 30 psi. FIG. 1 shows the dissolution profile of ascorbic acid coated with polyethylene wax under various conditions. The dissolution rate of ascorbic acid significantly decreased when coated with polyethylene wax at a grinding pressure of 20 psi and decreased further at 30 psi. This example demonstrates that the polyethylene wax deformed and spread as ascorbic acid was milled in the FEM. Higher grinding pressures further facilitated the deformation process due to their correlation with higher particle velocities and higher impact forces among the particles. FIG. 1 also shows that curing the polymer coating after the milling step significantly reduces the dissolution rate of ascorbic acid since it creates new drug surfaces. The present invention solves this problem by avoiding or minimizing the creation of new drug surfaces during the mixing and/or coating steps of the process.

Example 2

A deformable waxy polymer, carnauba wax, was used to coat ascorbic acid in a FEM. The carnauba wax had a median particle size of 15 μm and a lower Young's Modulus than polyethylene wax (<200 MPa). Ascorbic acid of three different volume averaged median particle sizes (341 μm, 192 μm, and 93 μm) was co-milled with 10 wt. % carnauba wax at three different pressures (10, 20, and 30 psi). Table 1 shows the coating results. High grinding pressures promoted high velocity particle collisions and caused better spreading of the polymer over the surface of the API core particles, as well as decreasing the coated particle size.

TABLE 1

Coating with carnauba wax at different grinding pressures

| Initial Particle Size (d50, μm) | Grinding Pressure | Final Particle Size (d50, μm) | % Increase in Surface Area* ($\mu m^2/g$) | Initial dissolution rate (—) |
|---|---|---|---|---|
| 341 | 0 | 341 | 0 | 4.053 |
| | 10 | 277.90 | 23 | 0.797 |
| | 20 | 123.69 | 176 | 0.756 |
| | 30 | 23.77 | 1335 | 0.645 |
| 192 | 0 | 192 | 0 | 7.764 |
| | 10 | 155.16 | 24 | 0.584 |
| | 20 | 47.49 | 304 | 0.641 |
| | 30 | 13.42 | 1331 | 0.469 |
| 93 | 0 | 93 | 0 | 9.16 |
| | 10 | 75.17 | 24 | 0.627 |
| | 20 | 29.85 | 212 | 0.586 |
| | 30 | 12.84 | 624 | 0.269 |

*Theoretical calculation based on the d50

It was also observed that the polymer coating improved with smaller initial particle sizes, see Table 1. This affect cannot be attributed to the extent of breakage of the ascorbic acid particles or the increase in surface area (as particles break, new surfaces were exposed that must be coated). As seen from the percent increase in surface area, smaller initial particle sizes actually required less newly created surfaces to be coated.

The quality of particle coating was influenced by two factors: the first factor being the number of particles interacting and colliding; the second factor being the initial core particle sizes. Since coating is accomplished through particle collision in the mill, more particle collisions resulted in better coating. As expected, larger core particles required lesser amounts of coating material to completely coat the particles as compared to the same weight core particles with smaller size.

Example 3

Figure 3:
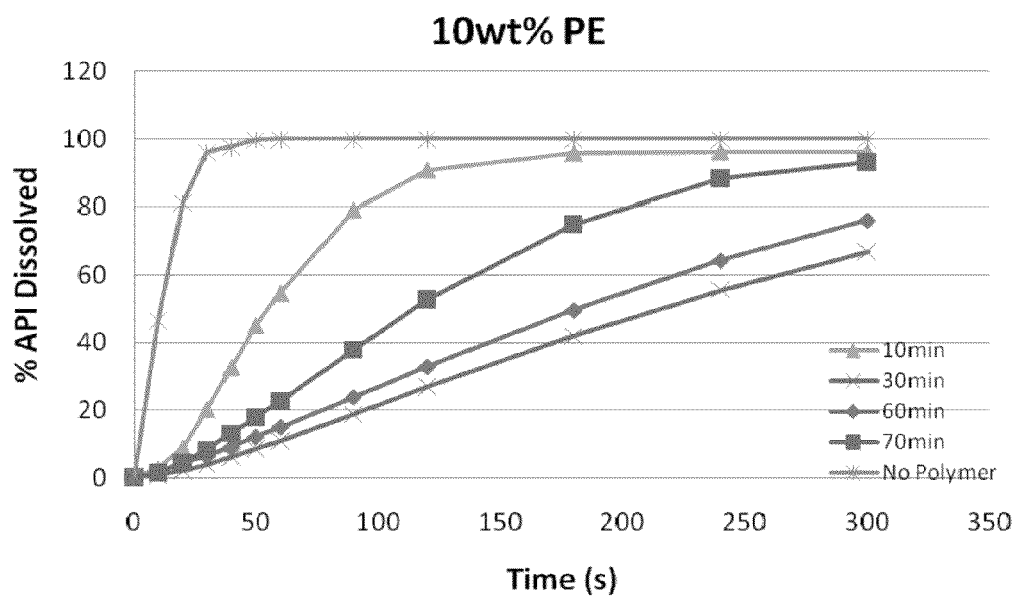
FIG. 3 shows dissolution profiles of ascorbic acid coated with PE wax employing various processing times.
Figure 4A:
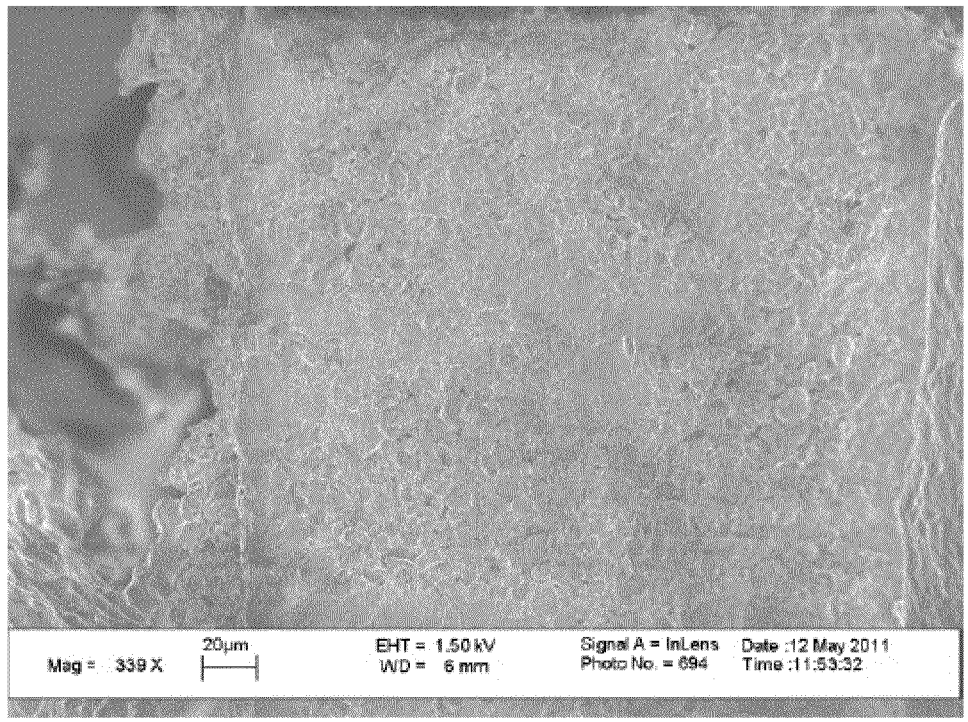
FIG. 4A is an SEM image of ascorbic acid coated with PE wax.
Figure 4B:
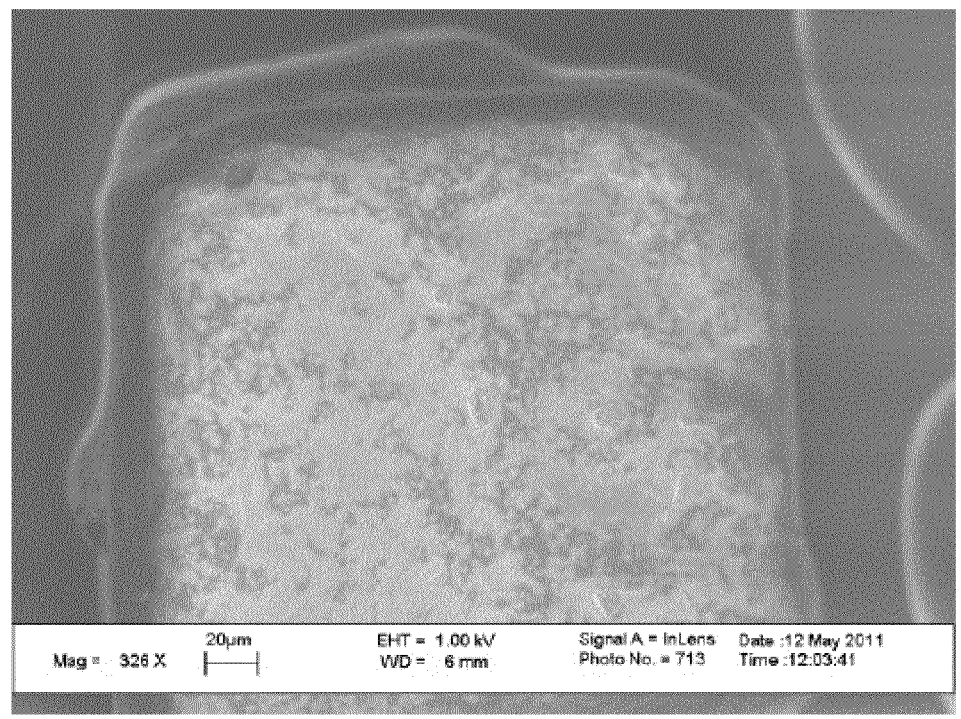
FIG. 4B is an SEM image of ascorbic acid coated with PE wax where the polymer layer is wearing away.

Ascorbic acid with a volume averaged median particle size of 344 μm was coated with 10 wt. % PE wax (median particle size 5.5 μm) using the LabRAM at 50 G's for various processing times. FIG. 3 shows that dissolution reaches a minimum rate at 30 minutes of processing time, corresponding to the best coating (FIG. 4A). Further mixing beyond 30 minutes increased the dissolution rate. The SEM image of FIG. 4B reveals that "overprocessing" or processing at times greater than 30 min caused the polymer layer to wear away or erode. This "over processing" may be due to some attrition/breakage, which can be avoided by using lower mixing intensities.

Example 4

Figure 5:
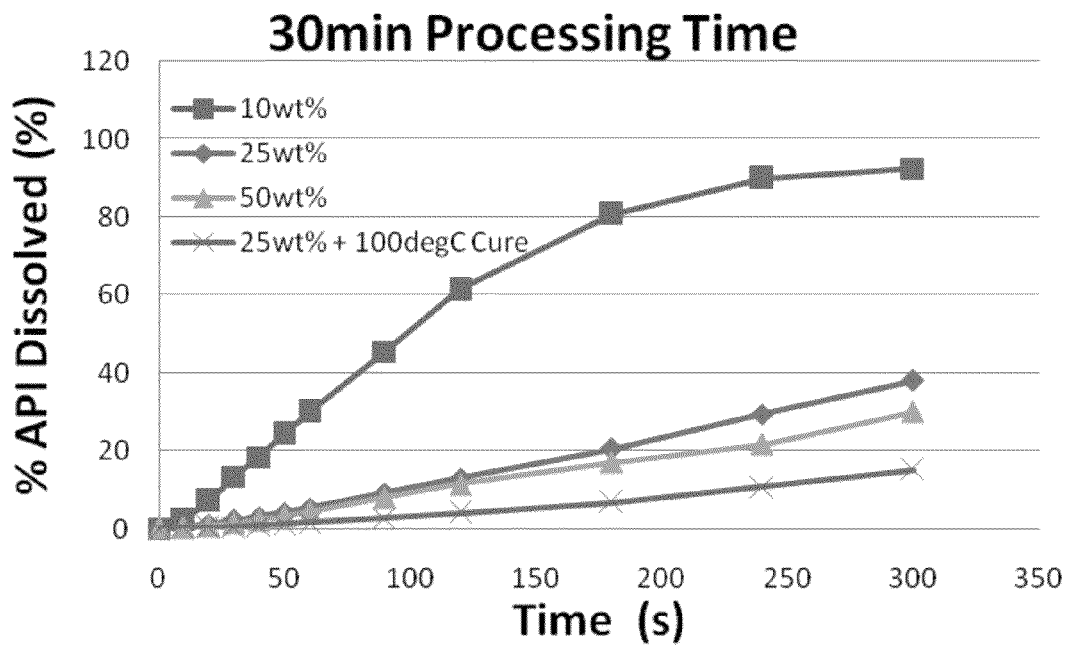
FIG. 5 shows dissolution profiles of ascorbic acid coated with PE wax at various loadings.

Various amounts of PE wax (median particle size 5.5 μm) were coated onto ascorbic acid with a volume averaged median particle size of 344 μm using a LabRAM at 100 G's for 30 minutes (FIG. 5). Dissolution test results showed a significant improvement when the polyethylene wax loading was increased from 10 wt. % to 25 wt. %. Only a minimal further improvement was observed by increasing the PE loading from 25 wt. % to 50 wt. %. Additional improvement in the coating (i.e. a reduction in dissolution rate) was achieved with curing. The cured samples showed very slow dissolution and a minimal amount of ascorbic acid dissolved at 1 minute.

Example 5

Figure 6:
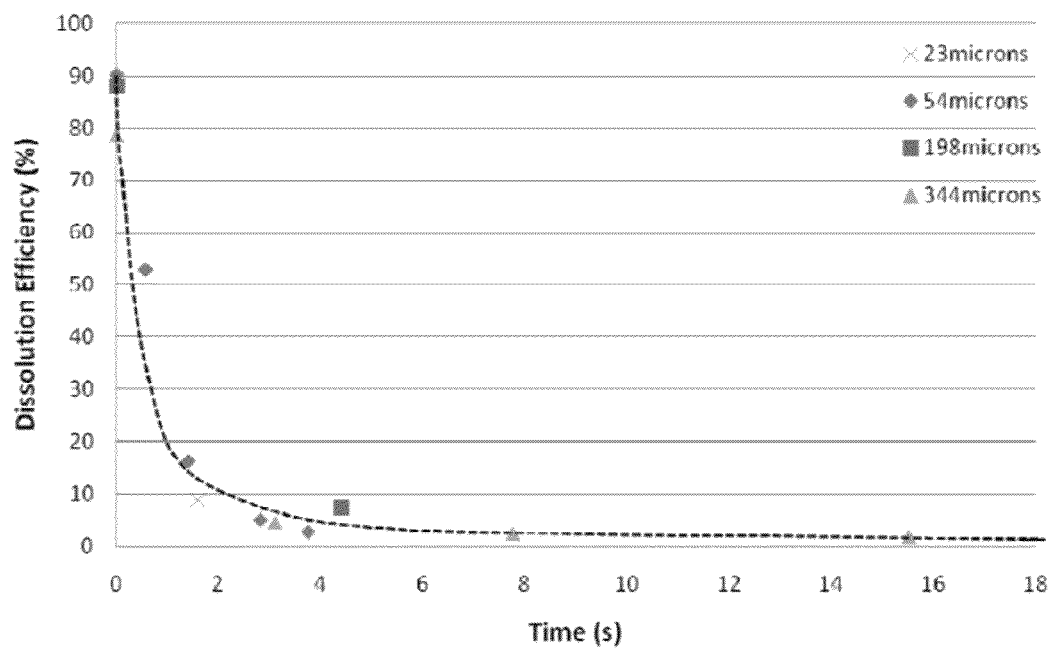
FIG. 6 shows the dissolution efficiency of ascorbic acid particles of various sizes coated with PE wax.

Ascorbic acid with various particle sizes was coated with PE wax using a LabRAM, as shown in FIG. 6. It was observed that dissolution of the ascorbic acid was controlled by the surface coverage of the PE wax for a wide range of API core particle sizes (23-344 μm). Here, dissolution efficiency is a measure of how fast the API dissolved. A dissolution efficiency of 0% corresponds to a complete arrest of dissolution and a dissolution efficiency of 100% corresponds to instantaneous dissolution.

Example 6

Figure 7:
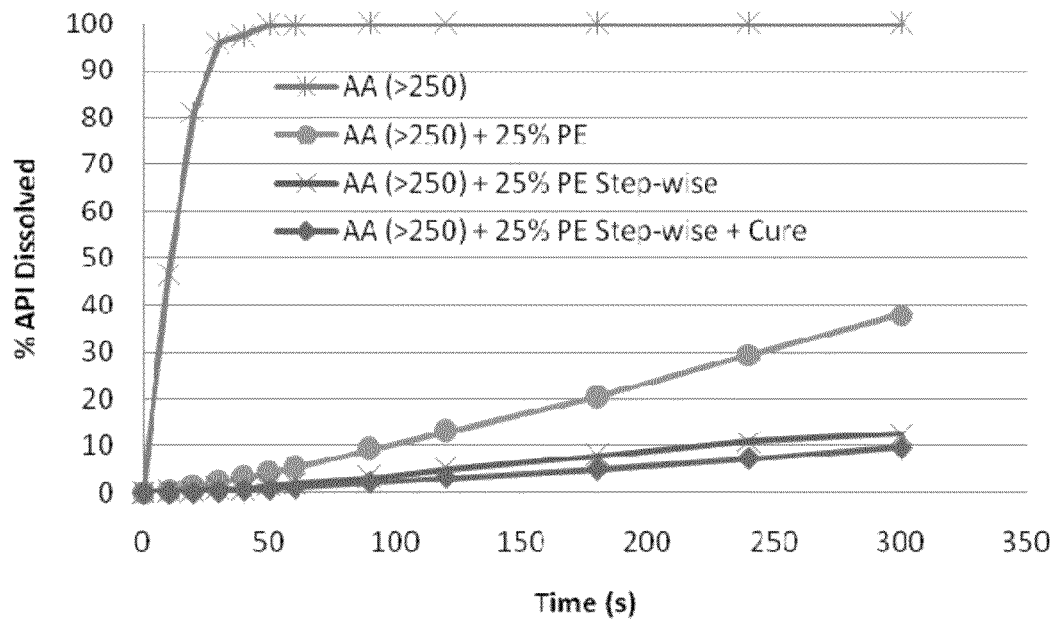
FIG. 7 shows dissolution profiles of ascorbic acid coated with PE wax by stepwise addition or single dose addition of PE wax.

The PE wax was added in a stepwise manner to ascorbic acid (AA) core particles having volume averaged median particle size greater than 250 μm (AA>250). In each step, 8.3% of PE wax was added to the ascorbic acid particles followed by acoustic mixing with LabRAM for 10 minutes at 40 G's. This process was repeated 3 times to achieve a total polymer loading of 25%. The stepwise coated ascorbic acid was cured at 110° C. for 20 minutes. The dissolution profile showed that coating in a stepwise manner significantly slowed the dissolution of ascorbic acid in comparison to a similar process adding all PE wax at once as shown in FIG. 7. This observation indicated that stepwise addition of coating particles may be more effective for taste masking than batchwise addition. Step-wise addition allows deformation of each layer rather than just the outer layer. This suggests that a 100% surface coverage should be added in each step of the stepwise addition. Curing of the polymer layer provided a small further reduction in the dissolution rate as shown in FIG. 7.

Example 7

Figure 8:
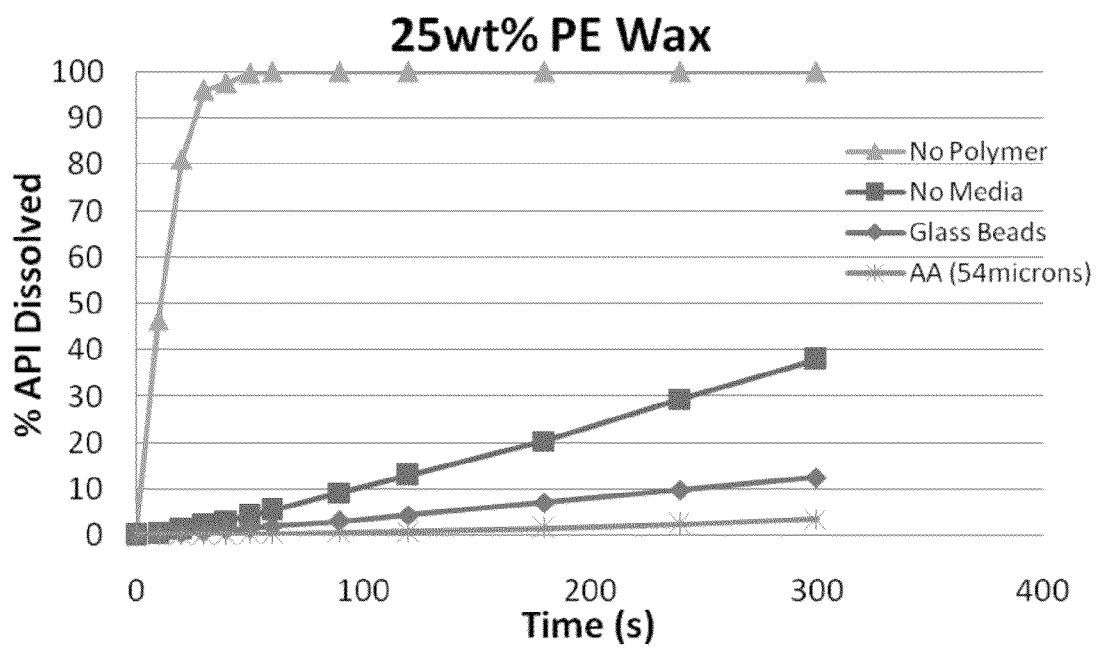
FIG. 8 shows dissolution profiles of ascorbic acid coated with PE wax in the presence of media.

Ascorbic acid with a volume averaged median particle size of 362 μm was coated with 25 wt. % PE wax both in the absence of, and in the presence of media particles (FIG. 8). A significantly lower dissolution rate of ascorbic acid was observed when it was as coated in the presence of either glass beads or additional smaller particles of ascorbic acid (volume averaged median particle size 54 μm). The latter process produced a coating which nearly arrested the dissolution of ascorbic acid up to 5 minutes for both sizes of the ascorbic acid particles used in the process. Similar effects were also observed when the coating was carried out with media particles such as glass beads with sizes different from the ascorbic acid particles.

Figure 9A:
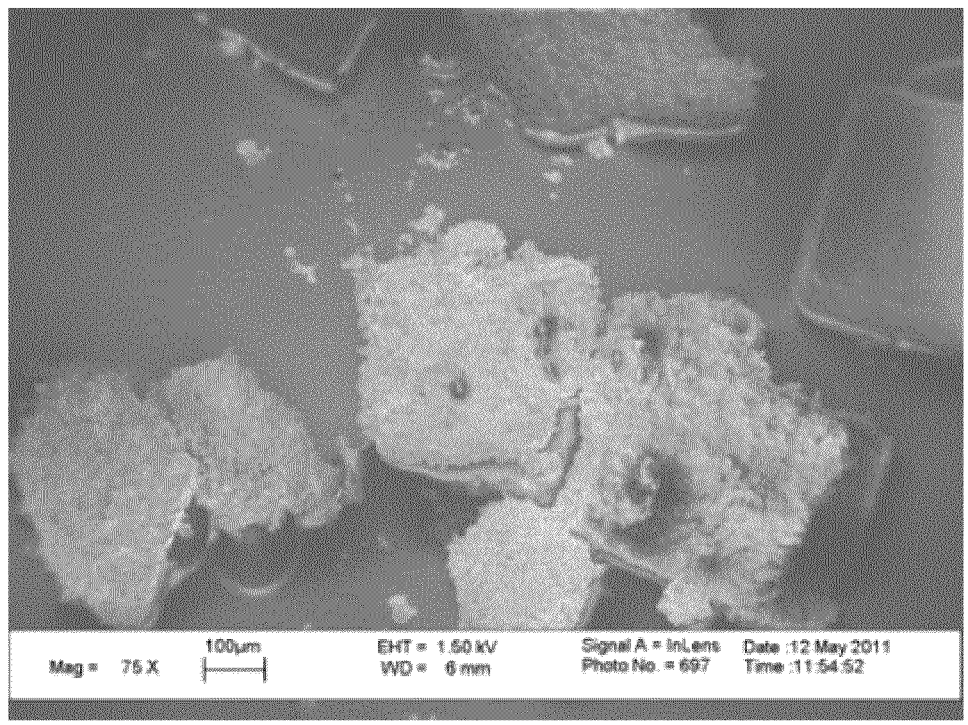
FIG. 9A is an SEM image of coarse ascorbic acid (362 μm) coated with PE wax (no media) at low magnification.
Figure 9B:
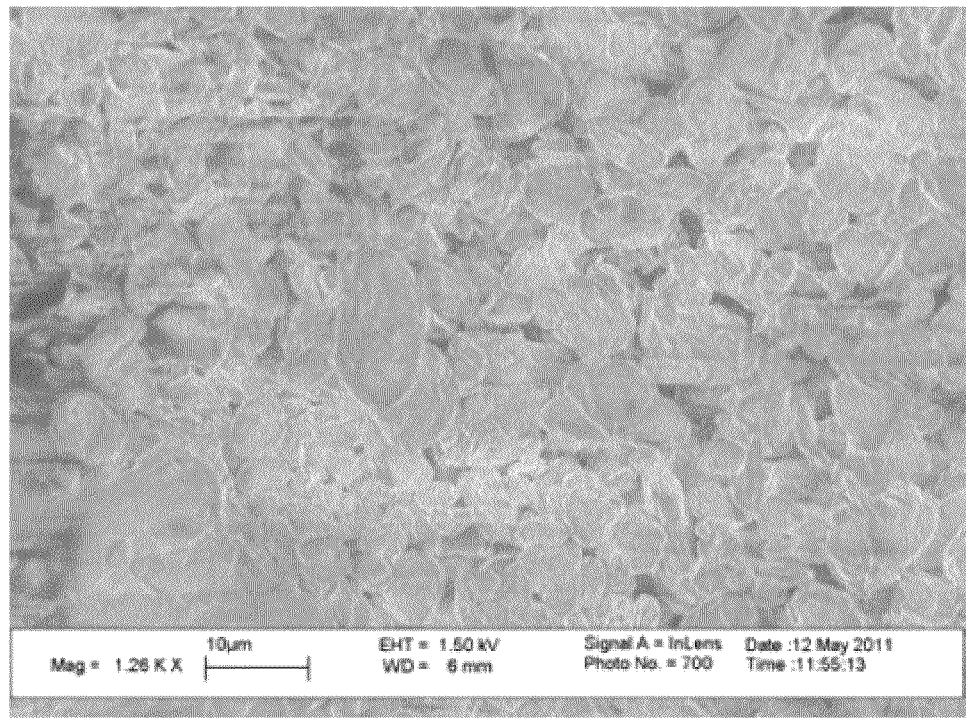
FIG. 9B is an SEM image of coarse ascorbic acid (362 μm) coated with PE wax (no media) at high magnification.
Figure 10A:
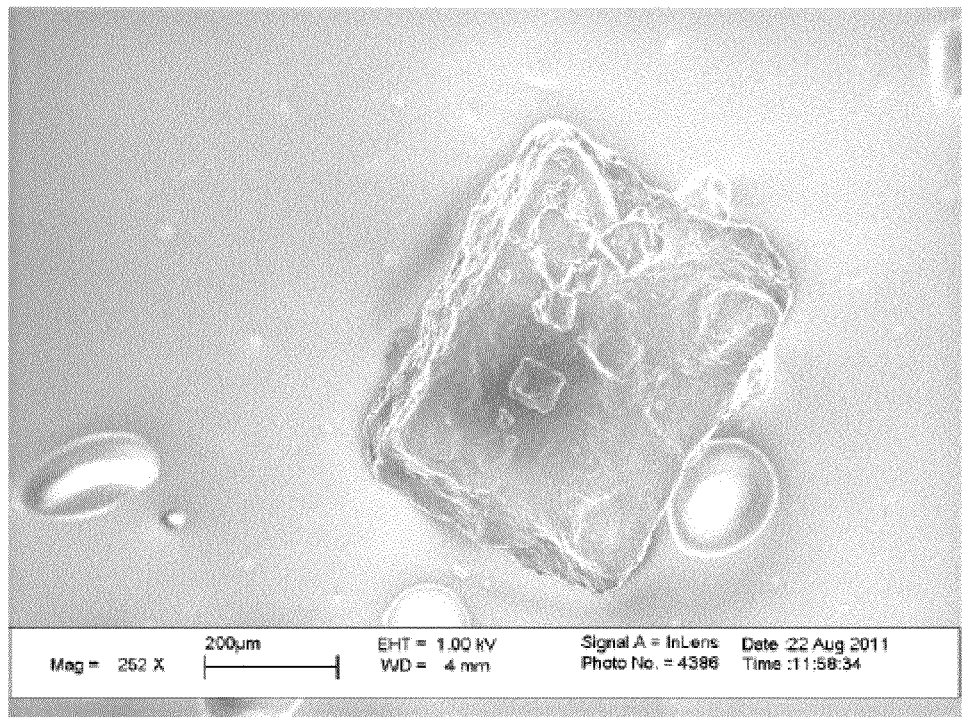
FIG. 10A is an SEM image of coarse ascorbic acid (362 μm) coated with PE wax (with media) at low magnification.
Figure 10B:
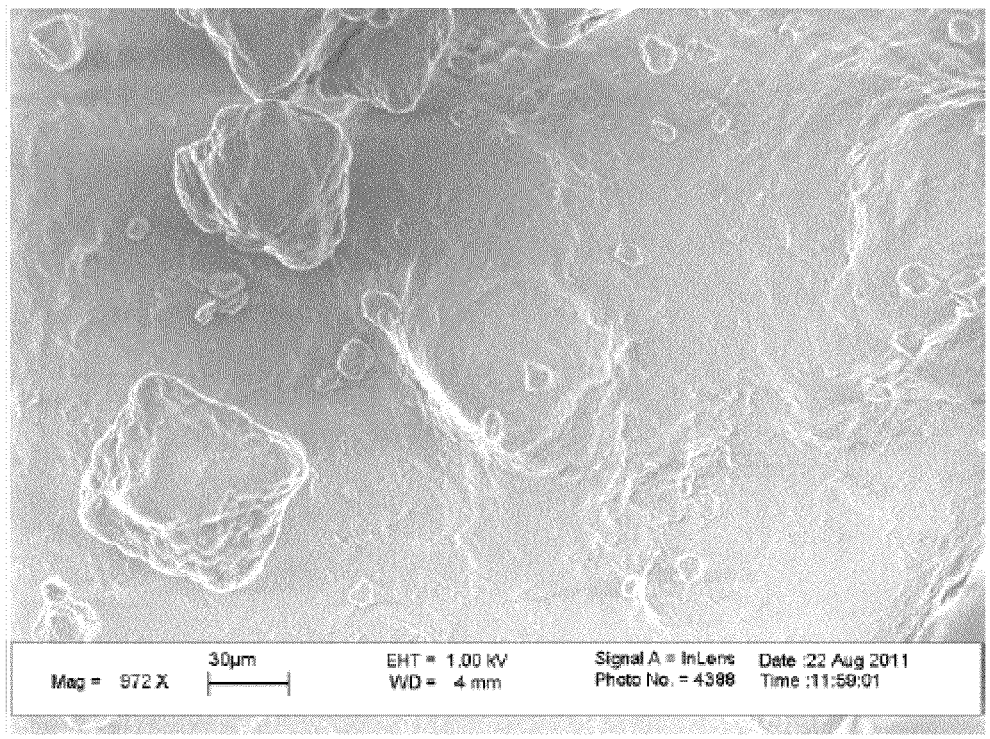
FIG. 10B is an SEM image of coarse ascorbic acid (362 μm) coated with PE wax (with media) at high magnification.
Figure 11A:
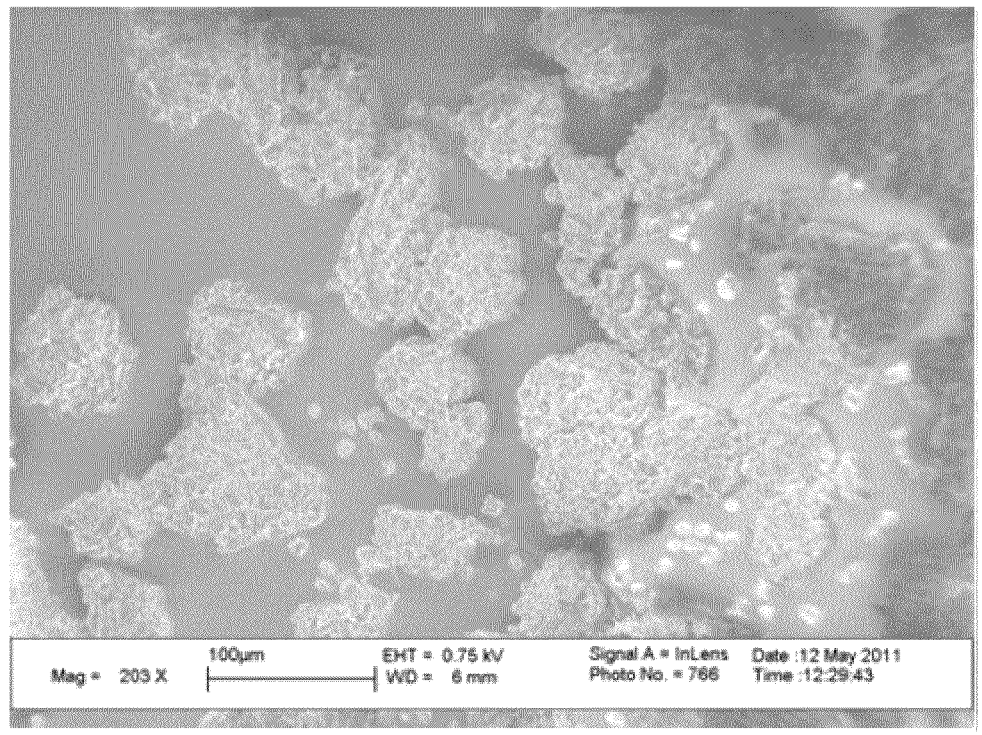
FIG. 11A is an SEM image of fine ascorbic acid (55 μm) coated with PE wax (no media) at low magnification.
Figure 11B:
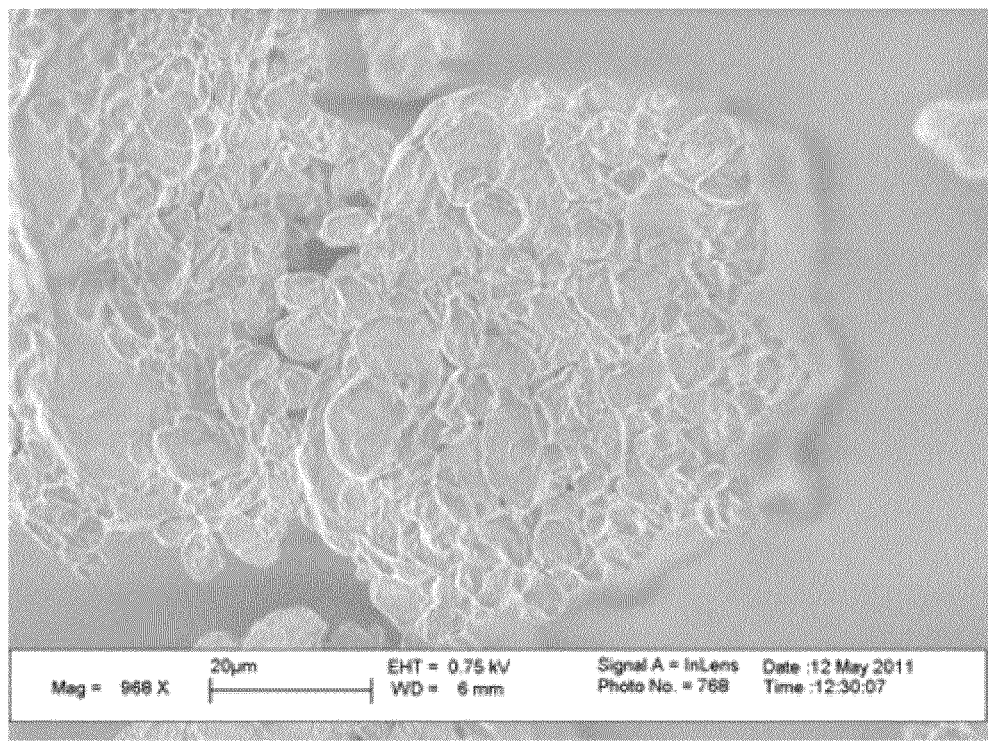
FIG. 11B is an SEM image of fine ascorbic acid (55 μm) coated with PE wax (no media) at high magnification.
Figure 12A:
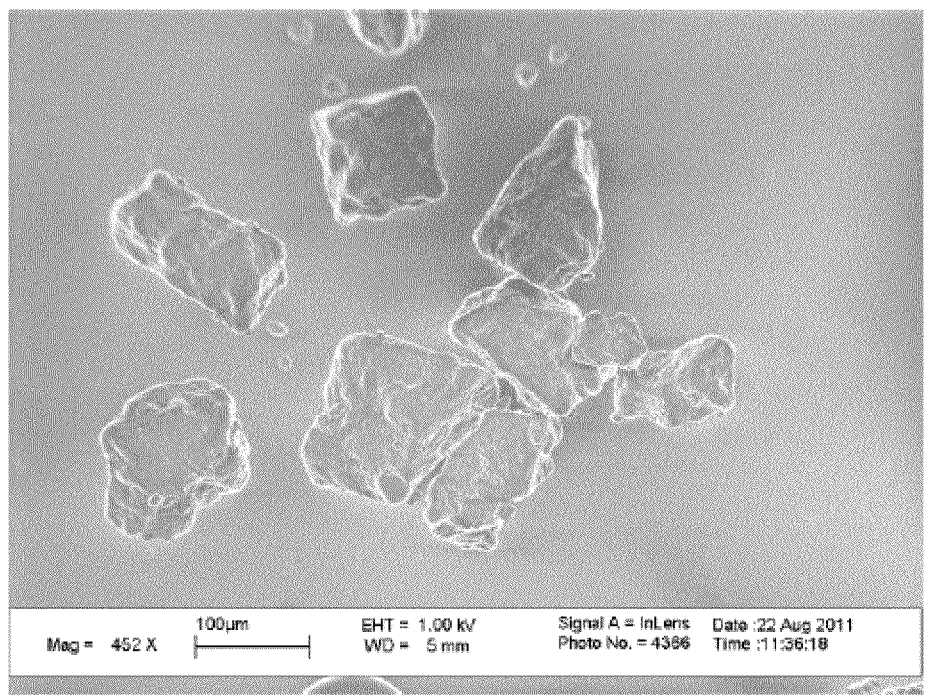
FIG. 12A is an SEM image of fine ascorbic acid (55 μm) coated with PE wax (with media) at low magnification.
Figure 12B:
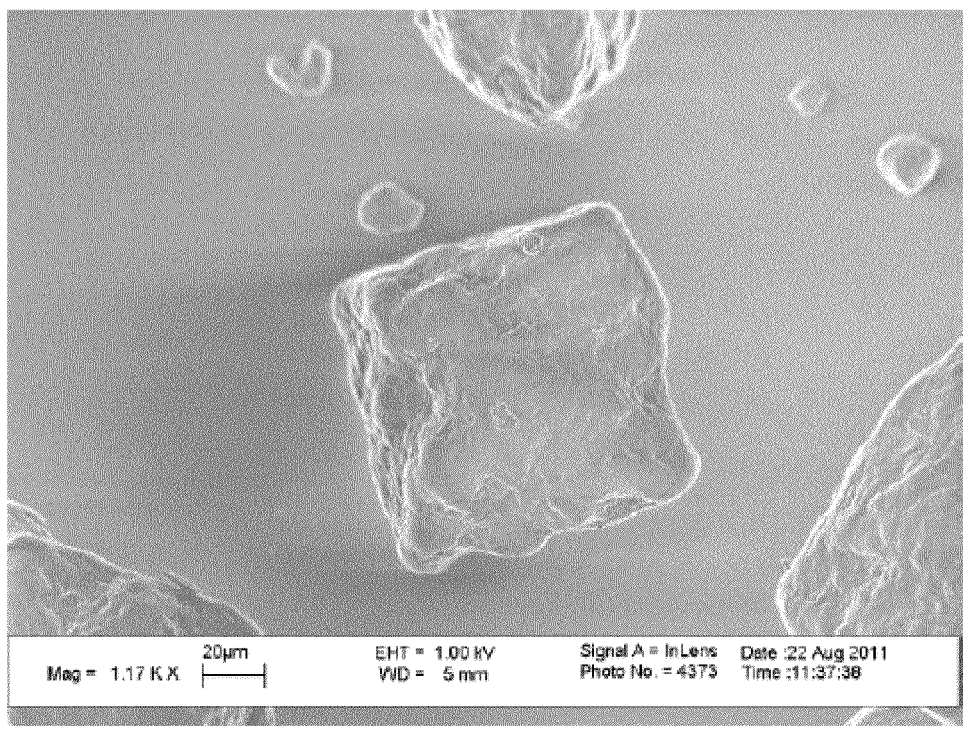
FIG. 12B is an SEM image of fine ascorbic acid (55 μm) coated with PE wax (with media) at high magnification.
Figure 13:
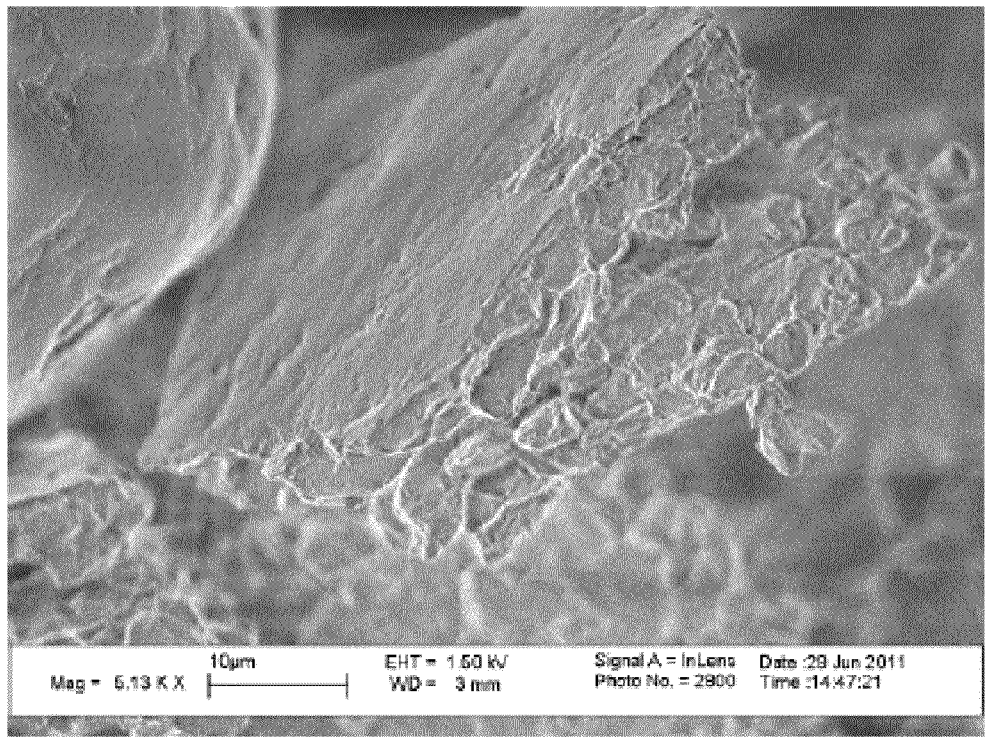
FIG. 13 is an SEM image of a piece of chipped away coating showing a continuous top PE polymer layer with several layers of discrete PE wax beneath.

These experiments created an excellent polymer coating on API core particles which nearly arrest API dissolution. The physical nature of the polymer layer was also affected by the presence of media particles. When no media particles were present, either coarse ascorbic acid particles (FIGS. 9A and 9B) or fine ascorbic acid particles (FIGS. 11A and 11B) were coated as discrete polymer layers. However, when media particles were used in the coating process, both coarse ascorbic acid particles (FIGS. 10A and 10B) and fine ascorbic acid particles (FIGS. 12A and 12B) were coated as continuous polymer layers. The continuous polymer layer may be a continuous top layer with several discrete layers beneath it (FIG. 13).

Example 8

Figure 14:
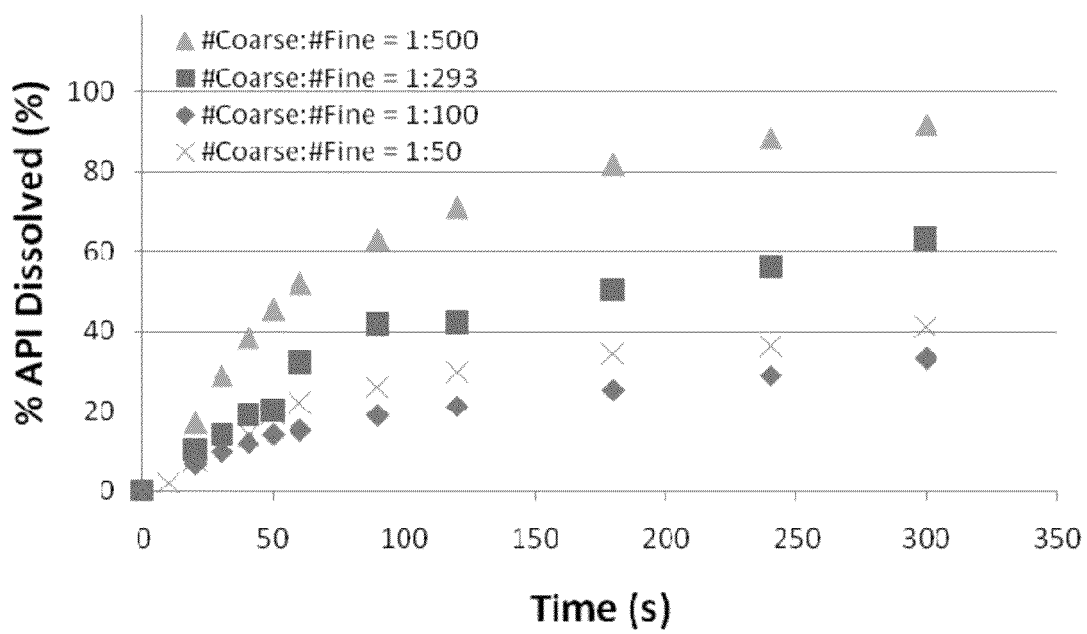
FIG. 14 shows dissolution profiles of ascorbic acid coated with PE wax in the presence of media at various concentrations.

To illustrate the impact of the amount of media particles on the coating process, ascorbic acid particles with a volume averaged median particle size of 362 μm were coated in the presence of ascorbic acid particles with a volume averaged median particle size of 55 μm using 25 wt. % PE wax. Ratios of coarse particles to fine particles of about 1:100 provided the best results (FIG. 14). The ratio may represent a balance between the number of particle collisions and the collision forces.

Example 9

Figure 15:
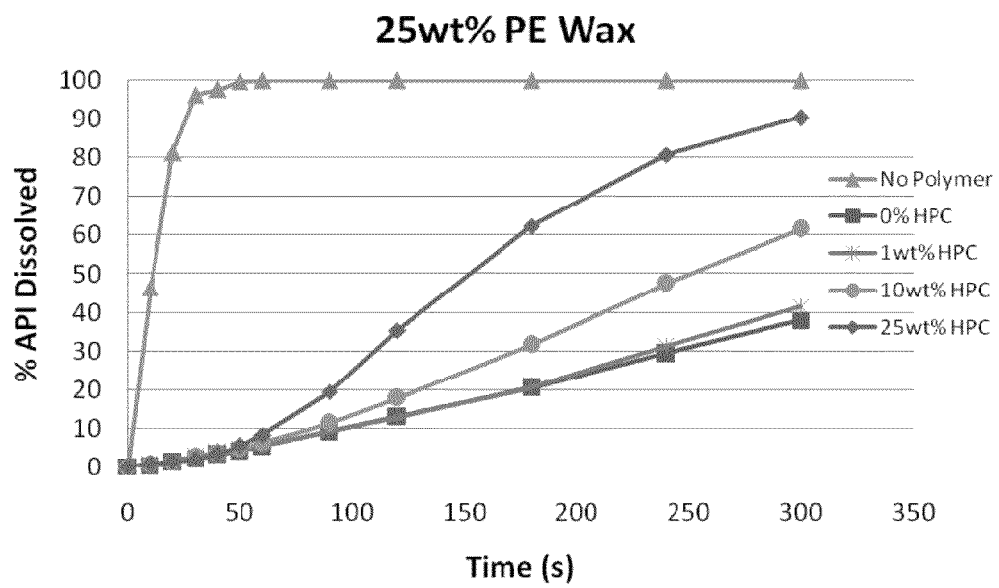
FIG. 15 shows dissolution profiles of ascorbic acid coated with PE wax and hydroxypropylcellulose (HPC) at various loadings.

To obtain a polymer coating that not only arrests the API dissolution at for a short time period (taste-masking), but also provides full release of the API at longer times up to 30 minutes (bioavailability), the hydrophilic polymer hydroxypropylcellulose (HPC) was used together with the hydrophobic PE wax to coat ascorbic acid particles. Ascorbic acid with a volume averaged median particle size of 372 μm was coated with 25 wt % PE wax and various, but smaller amounts of HPC with a median particle size of 13 μm. The resultant polymer layer contained particles of water soluble HPC and water insoluble PE in the continuous polymer layer. FIG. 15 shows that for the first 60 seconds, the dissolution rate was the same for all formulations with or without HPC. However, after 60 seconds, the dissolution rate increased with increasing amounts of HPC. The present example illustrates that after about a 60 second lag time for the HPC to wet and dissolve, the dissolution rate increased due to the surface area exposed by the dissolved HPC. This coating formulation is capable of nearly completely arresting the dissolution of ascorbic acid for the lag period, and providing almost complete dissolution of ascorbic acid within 5 minutes.

Example 10

Figure 16:
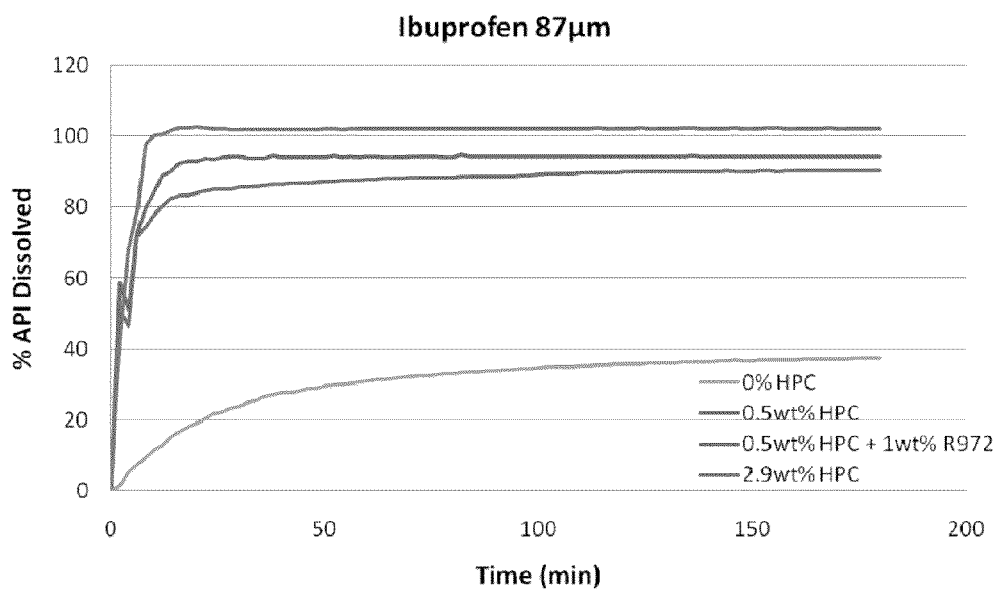
FIG. 16 shows dissolution profiles of ibuprofen (87 μm) coated with PE wax and hydroxypropylcellulose (HPC) at various loadings.

Ibuprofen with a volume averaged median particle size ($d_{50}$) of 87 μm ($d_{10}$=45 μm, $d_{50}$=87 μm, $d_{90}$=177 μm) was coated in a LabRAM at 100 G's for 30 minutes with 12.5 wt % PE wax (median particle size 5.5 μm) in the presence of 36 wt % sucrose with a median particle size of 402 μm. This corresponds to a particle number ratio of about 200 between ibuprofen and sucrose. Various amounts of HPC (0 wt. %, 0.5 wt. %, or 2.9 wt. %) were added to allow for full release of the API. The dissolution profiles are shown in FIG. 16. The formulation with 0% HPC yielded excellent taste masking with no bitter sensation or throat burn, but less than 2% API was dissolved in 2 minutes. With 0.5 wt. % HPC added, coated ibuprofen particles exhibited excellent taste-masking with the dissolution rate improved to a release of 90% of the API in 2 minutes. With 2.9 wt. % HPC, the ibuprofen was taste masked only up to 30 seconds and the dissolution test showed 100% API released in 2 minutes.

Ibuprofen particles coated with a formulation of 12.5 wt. % PE and 0.5 wt. % of HPC were then mixed with 1 wt. % of Aerosil R972 silica in order to improve the flowability of the taste-masked pharmaceutical formulation. The angle of repose improved from 51.1° to 40.2°, confirming a significant improvement in the powder flow. Additionally, the dissolution profile of the coated ibuprofen particles was not affected by the silica.

After the media particles (sucrose) were removed, the coated ibuprofen was further separated into fine and coarse fractions using a 63 μm sieve. Both fine and course fractions were found to be completely tasteless, which showed that the ibuprofen particles could indeed be taste masked over a fairly wide range of sizes.

Example 11

Ibuprofen particles with a wide size distribution (span 1.95, $d_{10}$=24 μm, $d_{50}$=70 μm, $d_{90}$=160 μm) were coated with PE wax and HPC particles (12.5 wt. % PE and 0.5 wt. % of HPC). This example illustrates the effect of size distribution of the API core particles on the taste masking efficiency of the solventless coating process. Using the same coating conditions as described in Example 10, the PE wax was added in a stepwise manner, i.e. adding half of the coating material to the ibuprofen and media particles, processing for 30 minutes and then adding the second half of the coating material for another 30 minutes of processing. This stepwise addition of PE wax allowed the ibuprofen to be well taste masked. The ibuprofen was then separated into 5 cuts by sieving (<38, 38-63, 63-90, 90-125, >125). Taste tests indicated that all size cuts were well taste masked except for the finest fraction.

Example 12

Figure 17:
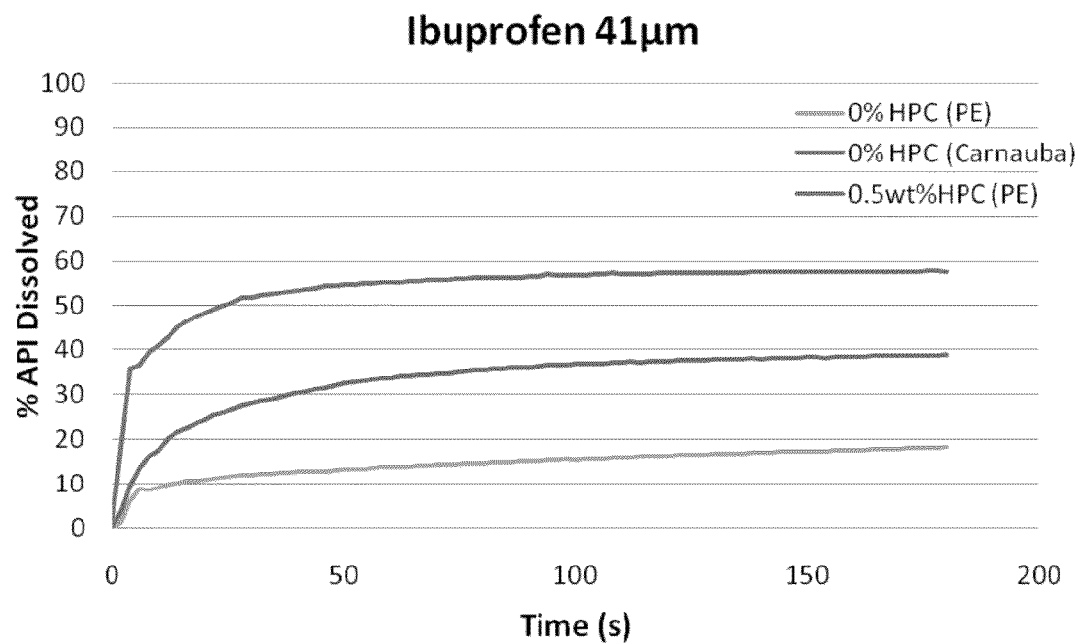
FIG. 17 shows dissolution profiles of ibuprofen (41 μm) coated with PE wax and HPC at various loadings.

Ibuprofen particles with a volume averaged median particle size of 41 μm (ibu-41) were coated by the same procedure as Example 10. Ibuprofen was coated in a LabRAM with 25 wt. % PE wax (median particle size 5.5 μm) in the presence of 31 wt. % sucrose ($d_{50}$ 235 μm). This corresponds to a particle number ratio of about 200 between ibuprofen and sucrose. The dissolution results are shown in FIG. 17. The formulation with 0% HPC resulted in excellent taste-masking with no bitter taste or throat burn. However, the dissolution was extremely slow with a release of API of less than 1.5% in 2 minutes and less than 20% in three hours. Adding 0.5 wt. % HPC to the formulation resulted in a slightly bitter taste and a slight but noticeable throat burn. However, dissolution was still slow and incomplete releasing less than 60% API in three hours. This may be due to the fact that the size of the ibuprofen is approaching the size of the HPC (13 μm), making it difficult to include the HPC in the coating layer. HPC is known to be a relatively fast dissolving polymer particularly at these small sizes. In addition, to attain both taste masking and complete dissolution, another type of additive may have to be added, either of a smaller size (~5 μm) or of a slower dissolving nature.

Example 13

Figure 18:
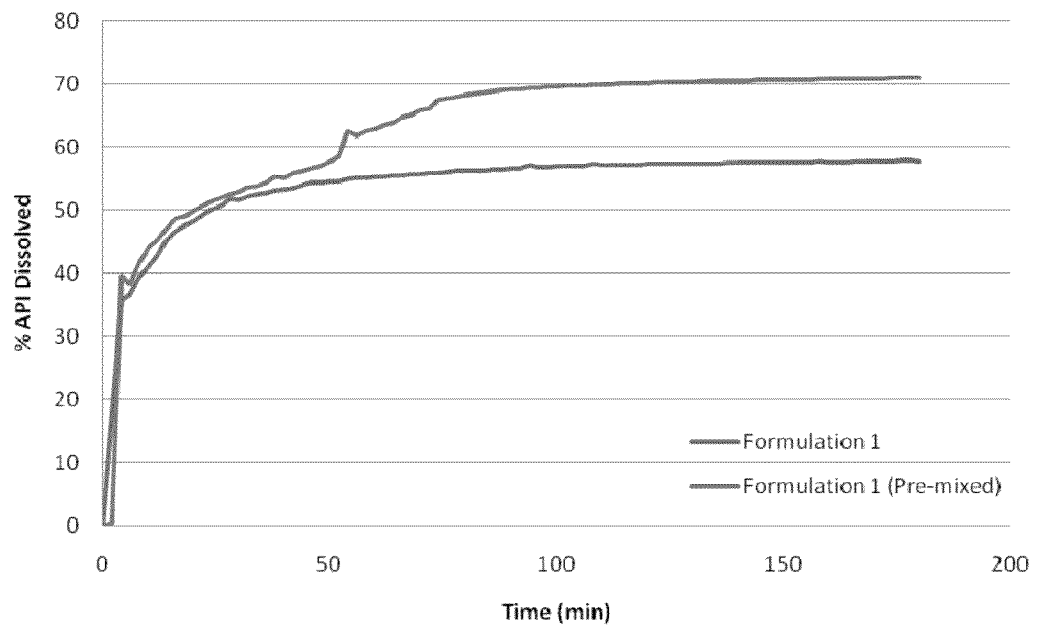
FIG. 18 shows dissolution profiles of ibuprofen coated with PE wax and HPC with and without enhanced premixing.

The HPC particles were pre-blended with the PE wax particles in appropriate proportions, with the LabRAM at 100G's for 1 minute. These pre-blended powders were then added to the ibuprofen particles and media particles. The coating process was the same as Example 12. FIG. 18 shows that preblending can be used to significantly increase the release of the ibuprofen, however complete release was still not achieved in three hours. This may be due to the fact that the hydrophobic PE wax particles may cover some of the hydrophilic HPC particles. As a result, the HPC was not capable of producing sufficient holes in the polymer coating layer necessary to achieve complete release.

Figure 19:
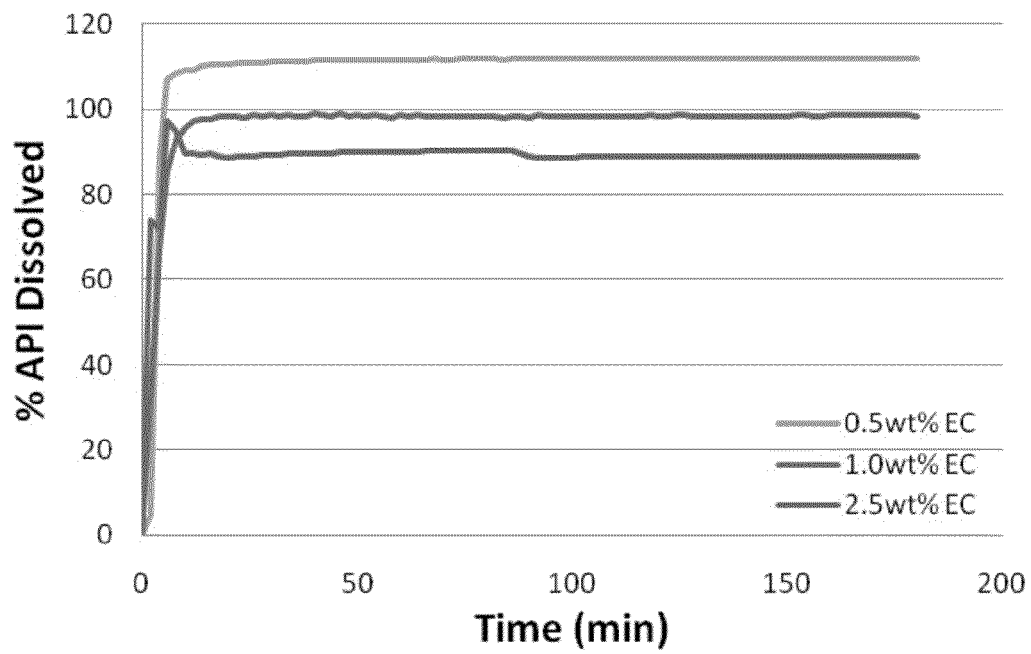
FIG. 19 shows dissolution profiles of ibuprofen with or without ethyl cellulose in the PE wax coating.

Another hydrophilic polymer, ethyl cellulose (EC with $d_{50}$=17 μm), was used to replace HPC in the coating process. Ibuprofen particles were coated with a mixture of PE wax and EC in the presence of sucrose media particles ($d_{50}$=235 μm), in the concentrations described in Table 2 below. Nearly complete release was achieved with all coating formulations (FIG. 19). The difference in the dissolution profiles between coating formulations using HPC and ethyl cellulose may be due at least partially to the difference in size (HPC with $d_{50}$=13 μm and EC with $d_{50}$=17 μm). The larger EC particles could not be easily covered by the wax particles (the wax layer is expected to be 11 μm thick) and therefore complete release was achieved. Even though all coating formulations achieved nearly complete release, only the lowest EC loading was capable of adequately taste masking the ibuprofen. Higher EC loadings allowed faster penetration of the saliva through the coating layer.

TABLE 2

| Coating formulations that provide taste masking and release | | | |
|---|---|---|---|
| Component % | 0.5% EC | 1% EC | 2.5% EC |
| Ibu-41 | 31.1 | 31.1 | 31.1 |
| Sucrose (235) | 43.7 | 43.7 | 43.7 |
| PE | 24.7 | 24.2 | 22.7 |
| EC | 0.5 | 1.0 | 2.5 |
| Taste | Well | Poor | Poor |

Two other hydrophilic polymers: commercially available lactose powders (Sorbolac 400=8 μm and Granulac 230=18 μm), were also used with PE wax to coat ibuprofen particles ibu-41 (volume averaged median particle size of 41 μm). The lactose particles were pre-treated with Aerosil R972 (hydrophobic silica) to slow down the wetting and dissolution of the lactose particles. The lactose powder was pre-treated with silica for either 100% or 300% surface area coverage to produce a poorly wetting but soluble lactose particle (Table 3). The wetting of the silica coated lactose was qualitatively assessed by placing a small amount of the coated lactose in deionized water to see if the lactose powder could wet and eventually submerge below the water's surface. It was observed that only Granulac 230 pre-treated with 100% SAC of Aerosil R972 offered sufficient wettability to submerge below the surface.

TABLE 3

R972 silica concentrations that produced poorly wetting lactose powders

|  | Silica Concentration for 100% SAC | Silica Concentration for 300% SAC |
|---|---|---|
| Sorbolac 400 (8 μm) | 1.17 | 3.51 |
| Granulac 230 (18 μm) | 0.55 | 1.65 |

*All powders were dry coated at 75 G's for 5 minutes

Figure 20:
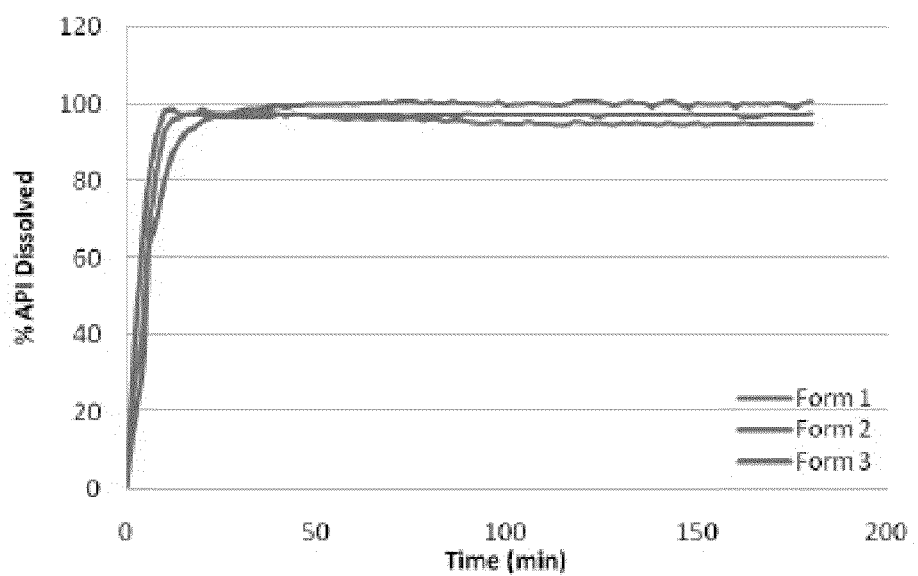
FIG. 20 shows dissolution profiles of formulations of Silica coated lactose (Sorbolac 400 with 100% SAC, Sorbolac 400 with 300% SAC and Granulac 230 with 300% SAC) blended with PE wax.
Figure 21:
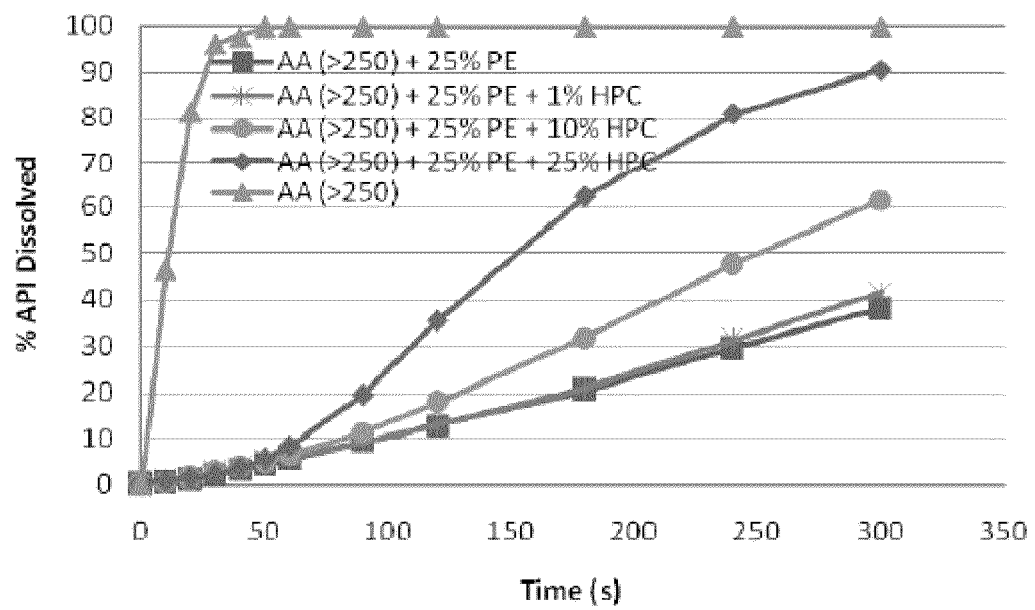
FIG. 21 shows dissolution profiles of ascorbic acid coated with PE wax and HPC at various loadings.

Silica coated lactose (Sorbolac 400 with 100% SAC, Sorbolac 400 with 300% SAC and Granulac 230 with 300% SAC) was blended with PE wax to achieve a final lactose concentration of 0.5% in the total system as described in Table 4. All coating formulations achieved nearly complete release of the API, however only Formulation 1, where Sorbolac 400 was coated with silica at 300% SAC, was well taste masked (see FIG. 20).

TABLE 4

Coating formulations with silica coated lactose

| Component | Formulation 1 (300% SAC of R972 on 8 μm) | Formulation 2 (100% SAC of R972 on 8 μm) | Formulation 3 (300% SAC of R972 on 18 μm) |
|---|---|---|---|
| Ibu-41 | 31.1 | 31.1 | 31.1 |
| Sucrose (235) | 43.7 | 43.7 | 43.7 |
| PE | 24.7 | 24.7 | 24.7 |
| Lactose | 0.5 | 0.5 | 0.5 |
| Taste | Well | Poor | Poor |

*Coated at 100 G's for 1 hour

Example 14

The acoustic mixing process of the present invention did not cause API core particle breakage or agglomeration. The size distribution of ibuprofen-87 (with volume averaged median particle size=87 μm) and ibuprofen-41 (with volume averaged median particle size=41 μm) was measured before and after coating (Table 5). The $d_{10}$, $d_{50}$, and $d_{90}$ showed an increase in particle size, but this was due to the addition of the polymer layer. This is confirmed by SEM images where no agglomeration of API particles was observed. Here, the coating formulation for ibuprofen-87 was the formulation 2 in Table 6 and coating formation for ibuprofen-41 is the formulation 5 in Table 7.

TABLE 5

Size distribution of API particles before and after polymer coating in LabRAM

|  | Host |  |  |
|---|---|---|---|
|  | d10 | d50 | d90 |
| Ibuprofen-87 before coating | 37.54 | 87.22 | 200.56 |
| Ibuprofen-87 after coating* | 42.48 | 95.62 | 215.45 |
| Ibuprofen-41 before coating | 14.31 | 40.88 | 86.28 |
| Ibuprofen-41 after coating^ | 20.41 | 52.17 | 95.85 |

Example 15

Various formulations were used to coat ibuprofen-87 (Table 6) and ibuprofen-41 (Table 7). The time at which 80% of ibuprofen was released was used as the criterion for evaluation because the best taste-masked formulations do not necessarily allow for fast or complete dissolution. Furthermore, it was observed that addition of Aerosil R972 silica on coated API core particles as a flow aid also increased the ease with which media particles (sucrose) and ibuprofen were separated. Here, sucrose is added as media in the coating process and is not part of the final formulation.

TABLE 6

Preferred formulations for coating ibuprofen-87

| Component | Formulation 1 | Formulation 2 | Formulation 3 |
|---|---|---|---|
| Ibuprofen* | 49.9 wt % | 49.8 wt % | 49.8 wt % |
| Sucrose^ | 37.4 wt % | 36.8 wt % | 36.8 wt % |
| PE Wax | 12.7 wt % | 12.9 wt % | 12.9 wt % |
| Soluble/Swellable additive | 0.0 wt % | 0.5 wt % (HPC) | 0.5 wt % (HPC) |
| Time of 80% Release | N/A | 12 min | 8 min |
| % Release at 3 hr | 37.5% | 90.3% | 94.3% |
| Additional Notes | — | HPC d50 = 13 μm | 1 wt % R972 Added after coating |

*Ibuprofen d50 = 87 μm
^Sucrose d50 = 402 μm

TABLE 7

Preferred formulations for coating ibuprofen-41

| Component | Formulation 1 | Formulation 2 | Formulation 3 | Formulation 4 | Formulation 5 |
|---|---|---|---|---|---|
| Ibuprofen* | 31.2 wt % | 25.7 wt % | 31.1 wt % | 31.1 wt % | 31.1 wt % |
| Sucrose^ | 43.9 wt % | 60.7 wt % | 43.7 wt % | 43.7 wt % | 43.7 wt % |
| PE Wax | 24.9 wt % | 13.6 wt % (Carnauba) | 24.7 wt % | 24.7 wt % | 24.7 wt % |
| Soluble/Swellable additive | 0.0 wt % | 0.0 wt % | 0.5 wt % (HPC) | 0.5 wt % (EC) | 0.5 wt % (Lac) |
| Time of 80% Release | N/A | N/A | N/A | 3-4 min | 10 min |
| % Release at 3 hr | 18.4% | 38.9% | 71.0% | 100% | 100% |
| Additional Notes | — | — | HPC was pre-mixed with PE wax | EC d50 = 17 μm | Lactose (8 μm) was pre-coated with 300% 5C R972 |

*Ibuprofen d50 = 41 μm
^Sucrose d50 = 235 μm

Example 16

Figure 22:
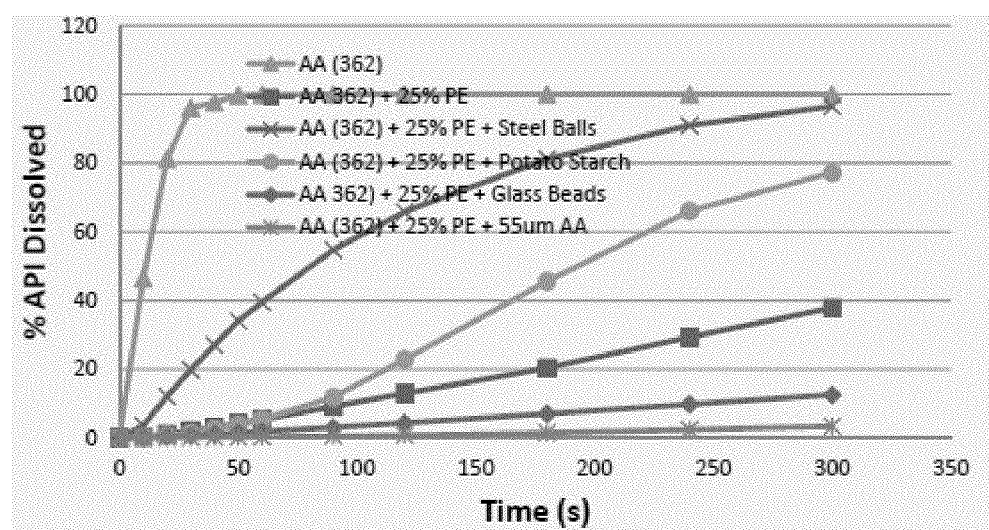
FIG. 22 shows dissolution profiles of ascorbic acid coated with PE wax using various media particles in the coating process.

Ascorbic acid particles (362 µm) were coated with PE wax 25 wt. % in the presence of various types of media particles using a LabRAM. All media concentrations were 25% by weight. The media particles included ⅛th inch stainless steel beads, 34 µm potato starch particles, 75 µm glass beads, 55 µm ascorbic acid (AA) particles. The high intensity collisions resulting from the heavy stainless steel balls (⅛th inch) led to attrition and poor dissolution. Visual observations show severe breakage of the 362 µm ascorbic acid particles. On the other hand, the low intensity collisions resulting from soft potato starch also led to poor coating. Better results were observed with 75 µm glass beads, which provided a significant reduction in the dissolution profile. Surprisingly 55 µm ascorbic acid led to even slower dissolution and did not suffer from the problem of potential contamination like the glass beads. See FIG. 22.

Example 17

Figure 23:
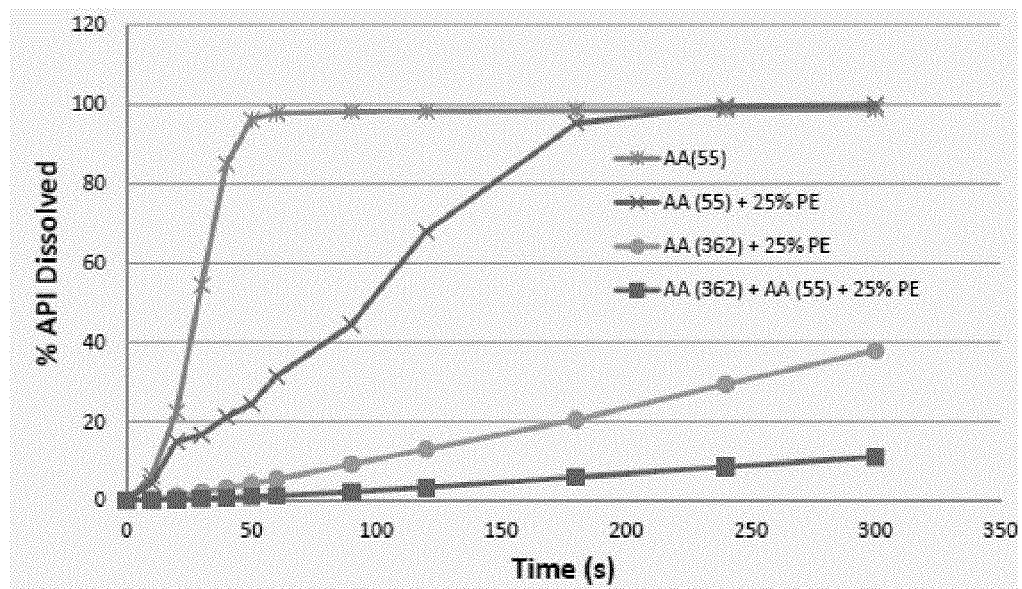
FIG. 23 shows dissolution profiles of ascorbic acid of different sizes coated with PE wax.

Coarse ascorbic acid particles (with a volume averaged median particle size of 362 µm) and fine ascorbic acid particles (with a volume averaged median particle size of 55 µm) were coated with 25% PE wax using LabRAM for 30 minutes at 100 G's. Dissolution profiles of the coated particles indicated that when coarse and fine particles were coated at the same time, superior results were achieved as compared to when the coarse and fine particles were coated separately (FIG. 23).

Figure 24A:
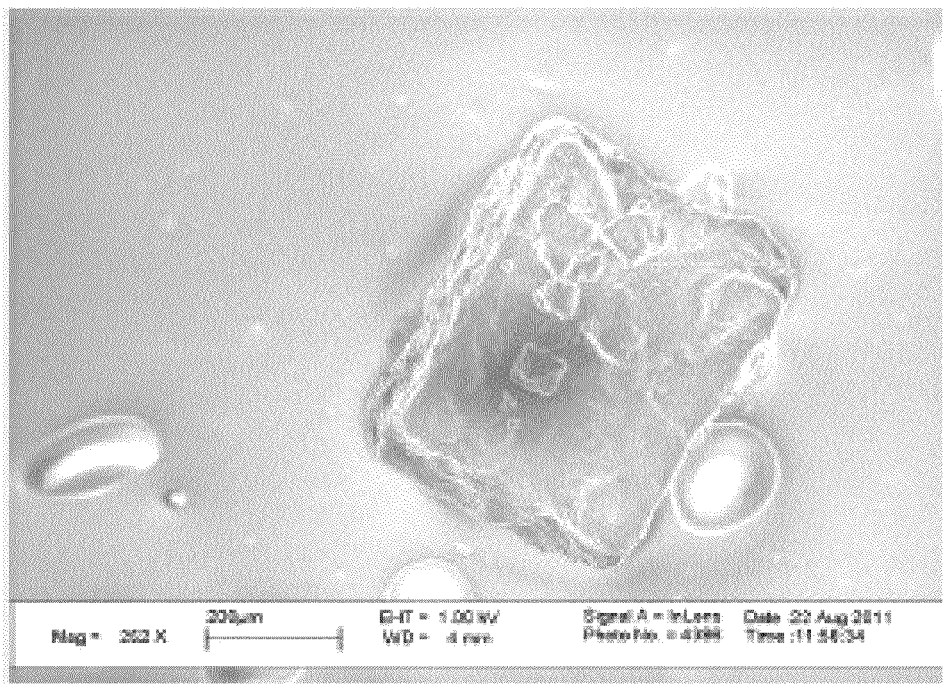
FIG. 24A is an SEM image of ascorbic acid particles with a continuous polymer layer at low magnification.
Figure 24B:
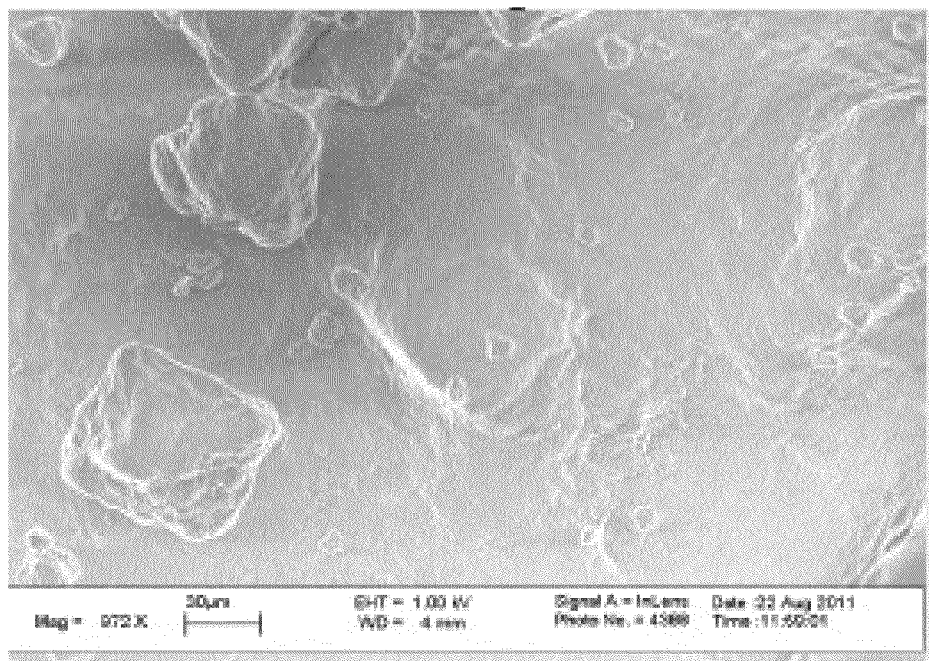
FIG. 24B is an SEM image of ascorbic acid particles with a continuous polymer layer at high magnification.
Figure 25A:
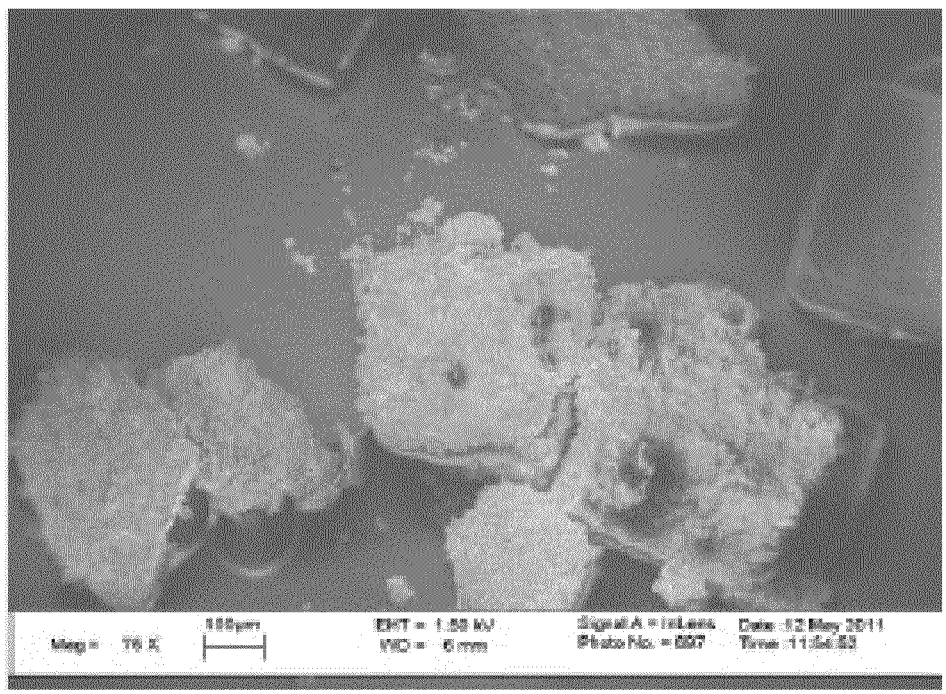
FIG. 25A is an SEM image of ascorbic acid particles with a discrete polymer layer at low magnification.

SEM images show that the use of media can provide a continuous surface without the use of curing (FIGS. 24A-24B), while when no media particles were added, the polymer coating is a discrete layer (FIGS. 25A-25B). The continuous polymer layer significantly decreased the dissolution rate and improved taste masking.

Figure 26:
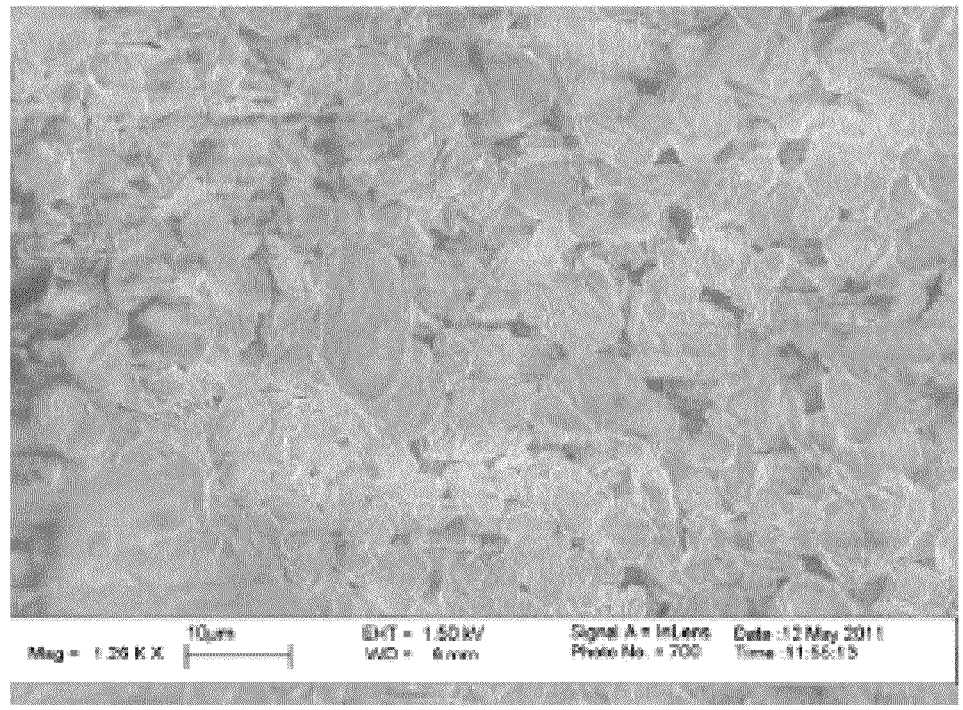
FIG. 26 shows dissolution profiles of ascorbic acid of different sizes coated with PE wax.
Figure 26:
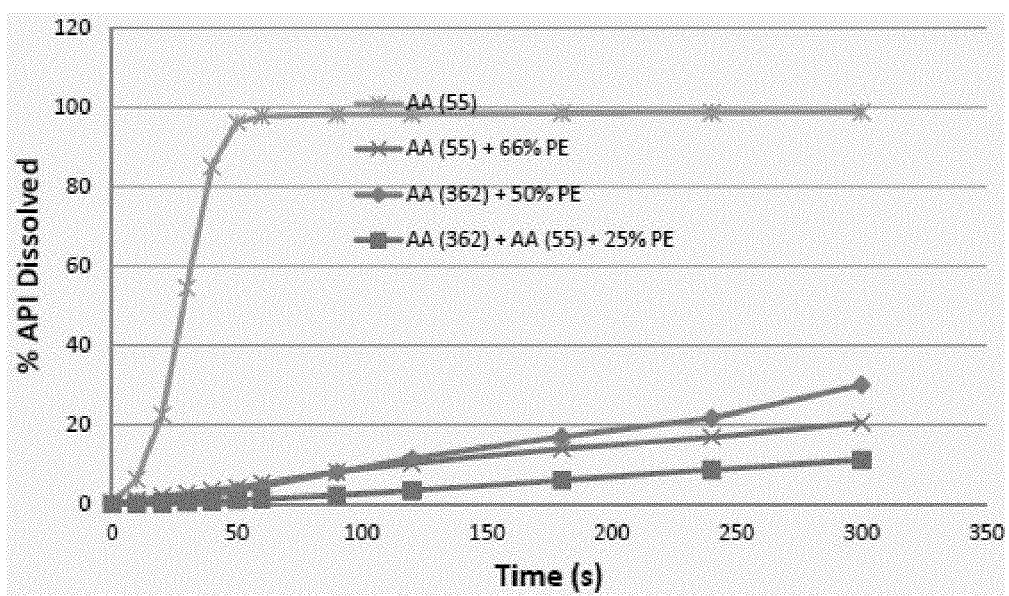

When no media particles were used, significantly higher polymer loadings were required to achieve high quality coatings (362 µm AA with 50% PE or 55 µm AA with 66% PE). This level of polymer loading resulted in a lowering of the overall potency of the pharmaceutical composition. When coarse (362 µm) and fine particles (55 µm) ascorbic acid were coated at the same time, lower PE loading can achieve the same reduction in dissolution time (FIG. 26).

Example 18

Figure 27:
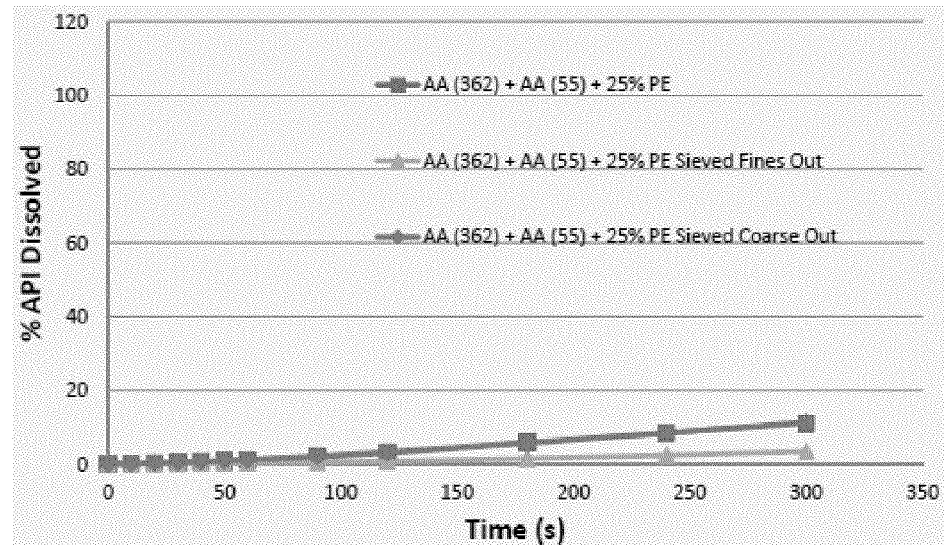
FIG. 27 shows dissolution profiles of ascorbic acid coated with PE wax.

Coarse ascorbic acid particles (with a volume averaged median particle size of 362 µm) and fine ascorbic acid particles (with a volume averaged median particle size of 55 µm) were coated with 25% PE wax using a LabRAM for 30 minutes at 100 G's. After coating the coarse and fine particles were separated by sieving and the dissolution profiles were compared among the fractions (FIG. 27). The fine particles and the unsieved powders had the same dissolution profile, while the coarse particles dissolved much slower than the fine particles and the unsieved powder.

Example 19

Figure 28:
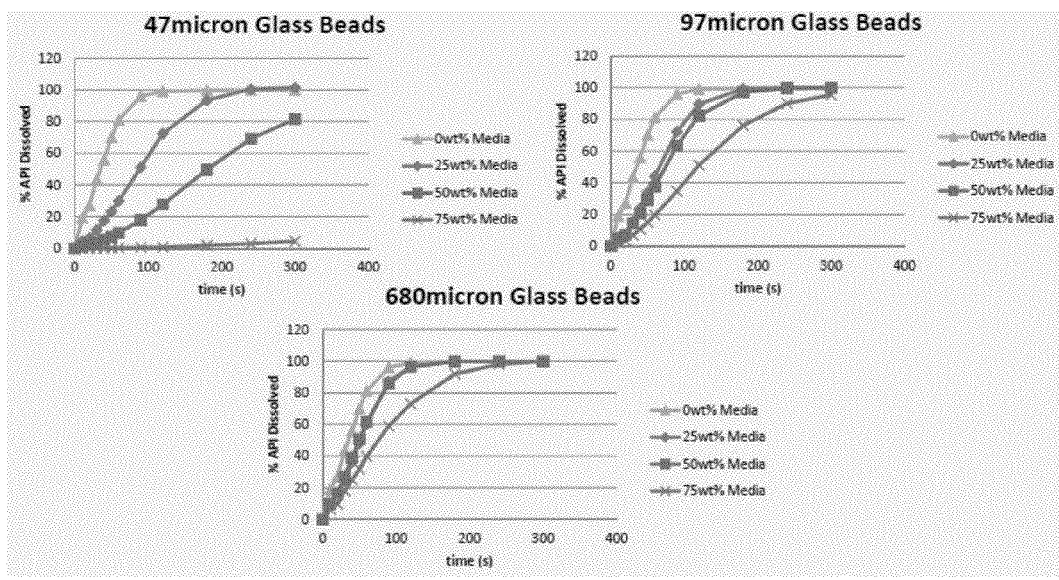
FIG. 28 shows dissolution profiles of ascorbic acid coated with PE wax in the presence of glass beads of different sizes.

Ascorbic acid particles with a volume averaged median particle size 354 µm were coated in the presence of glass beads of various sizes. The ascorbic acid particles were coated with 0.0363 g of PE wax per gram of ascorbic acid, which is equivalent to about two surface coverage multiples using a LabRAM for 1 hour at 100G's. Media particles were removed by sieving before the dissolution test. The results show that higher media concentrations and smaller media particle sizes significantly improved the coating and slowed down the dissolution of the ascorbic acid (FIG. 28).

Example 20

Ibuprofen ($d_{10}$=24, $d_{50}$=70, $d_{90}$=170) was coated with a blend of HPC (median particle size=9 µm) and PE Wax (median particle size=5.5 µm) in a weight ratio of 4:96. 13% of this polymer blend was coated onto the surface of the ibuprofen in the presence of edible 402 µm sucrose media particles. The polymer may be added in a single dose and coated with a LabRAM at 100G's for 30 minutes, or the polymer blend may be added in 2 steps (6.5% polymer and coated with a LabRAM at 100G's for 15 minutes, then add the other 6.5% polymer and coat with the LabRAM at 100G's for another 15 minutes).

Figure 29:
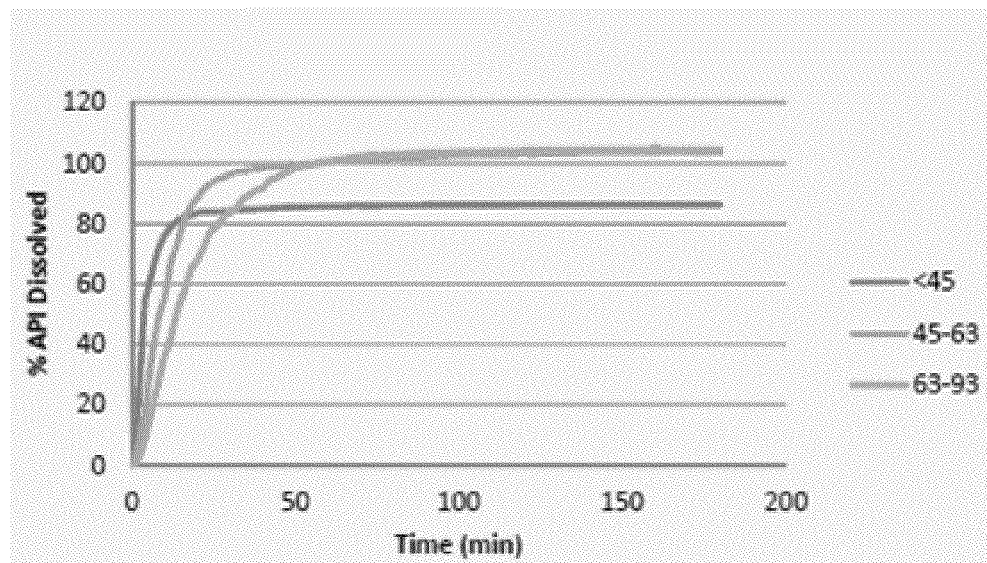
FIG. 29 shows dissolution profiles of ascorbic acid coated with PE wax that is separated into fractions by size.

The ibuprofen coated with polymer blend added in a single dose produced an unpleasant taste. The coated powder was sieved into 3 cuts: <45, 45-63, 63-90, all of which were poorly taste masked. On the other hand, ibuprofen coated with the polymer blend using stepwise addition was well taste masked. The coated powder was sieved into 3 cuts: <45, 45-63, 63-90, all of which were well taste masked, except for the finest cut (<45). After removing the finest particles, the coated ibuprofen powder was completely tasteless. Dissolution results showed that the finest particles had the fastest initial dissolution rate, which would introduce the unpleasant taste. However, the finest particles also did not completely dissolve after 3 hours. 85% release was achieved in 40, 18 and 32 minutes for <45, 45-63 and 63-93 sized cuts, respectively (FIG. 29).

Example 21

Figure 30:
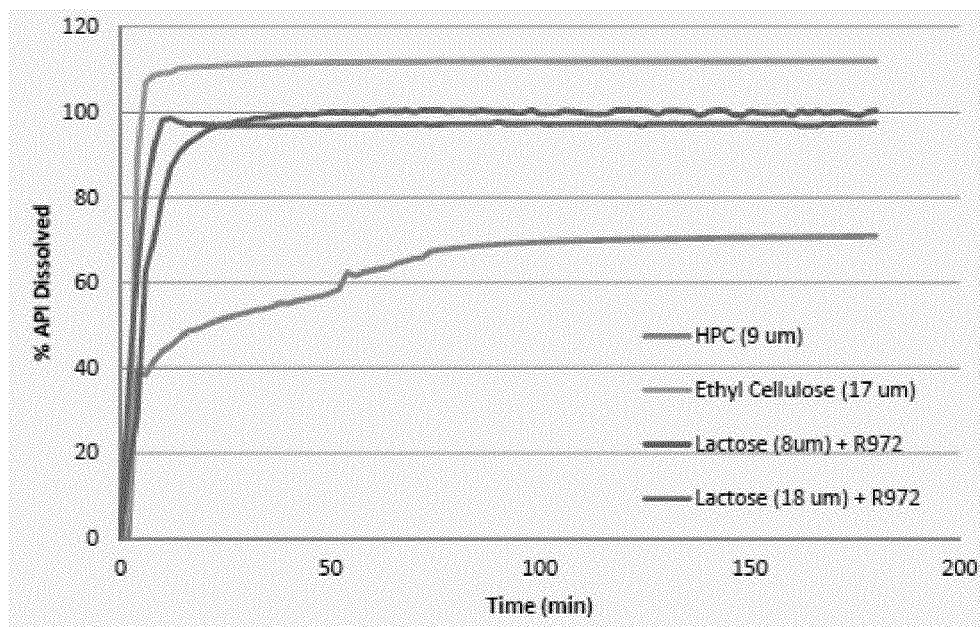
FIG. 30 shows dissolution profiles of ascorbic acid coated with PE wax and various hydrophilic polymers.

Ibuprofen particles with a volume averaged median particle size of 41 µm were coated with PE wax (median particle size 5.5 µm) as the hydrophobic polymer and various different polymers as the hydrophilic polymer at a loading of 96:4 (hydrophobic to hydrophilic). The hydrophilic polymer particles were HPC (9 µm), EC (17 µm), lactose (8 µm) dry coated with Aerosil R972, and lactose (18 µm) dry coated with Aerosil R972. The coating formulations with different hydrophilic polymers were all capable of taste masking the ibuprofen while still achieving fast release. Larger sized hydrophilic polymer particles offered slightly better dissolution than smaller sized ones (FIG. 30).

Example 22

In order to determine the effect of polymer content on the coating layer thickness after processing, 45 µm-63 µm 90 µm-125 µm, 150 µm-250 µm, 425 µm-500 µm, and 45 µm-500 µm sieve cuts of ascorbic acid were mixed with various amounts of PE wax (0-30 wt. %) and processed according to the conditions in Table 8. The processing conditions of Table 2 are not optimized, but offer a basis in which to understand the effect of polymer content on the final coating thickness. In experiments where glass beads are used, they were sieved out before size measurement.

TABLE 8

Sieve cuts and corresponding size statistics
for ascorbic acid, glass beads, and PE wax

|  | Sieve Cut | | |
| --- | --- | --- | --- |
|  | $x_{10}$ (μm) | $x_{50}$ (μm) | $x_{90}$ (μm) |
| Ascorbic Acid | | | |
| 425 μm-500 μm | 370.8 | 521.6 | 663.8 |
| 150 μm-250 μm | 146.5 | 232.4 | 304.5 |
| 90 μm-125 μm | 72.3 | 115.7 | 163.0 |
| 45 μm-63 μm | 23.4 | 56.8 | 83.8 |
| 45 μm-500 μm | 99.7 | 242.4 | 405.1 |
| Glass Beads | | | |
| 45 μm-53 μm | 38.9 | 47.0 | 58.7 |
| — | 532.0 | 662.5 | 816.6 |
| Polyethylene Wax | | | |
| — | 2.1 | 6.7 | 13.3 |

TABLE 9

Processing conditions

| Ascorbic Acid | Media | Media:Host Mass Ratio | Intensity (g's) | Processing Time (min) |
| --- | --- | --- | --- | --- |
| 425 μm-500 μm | 47.0 μm Glass beads | 3:1 | 100 | 20 |
| 150 μm-250 μm | — | — | 100 | 60 |
| 90 μm-125 μm | — | — | 100 | 240 |
| 45 μm-63 μm | 662.6 μm Glass beads | 1:2 | 100 | 240 |
| 45 μm-500 μm | — | — | 100 | 60 |

Figure 31:
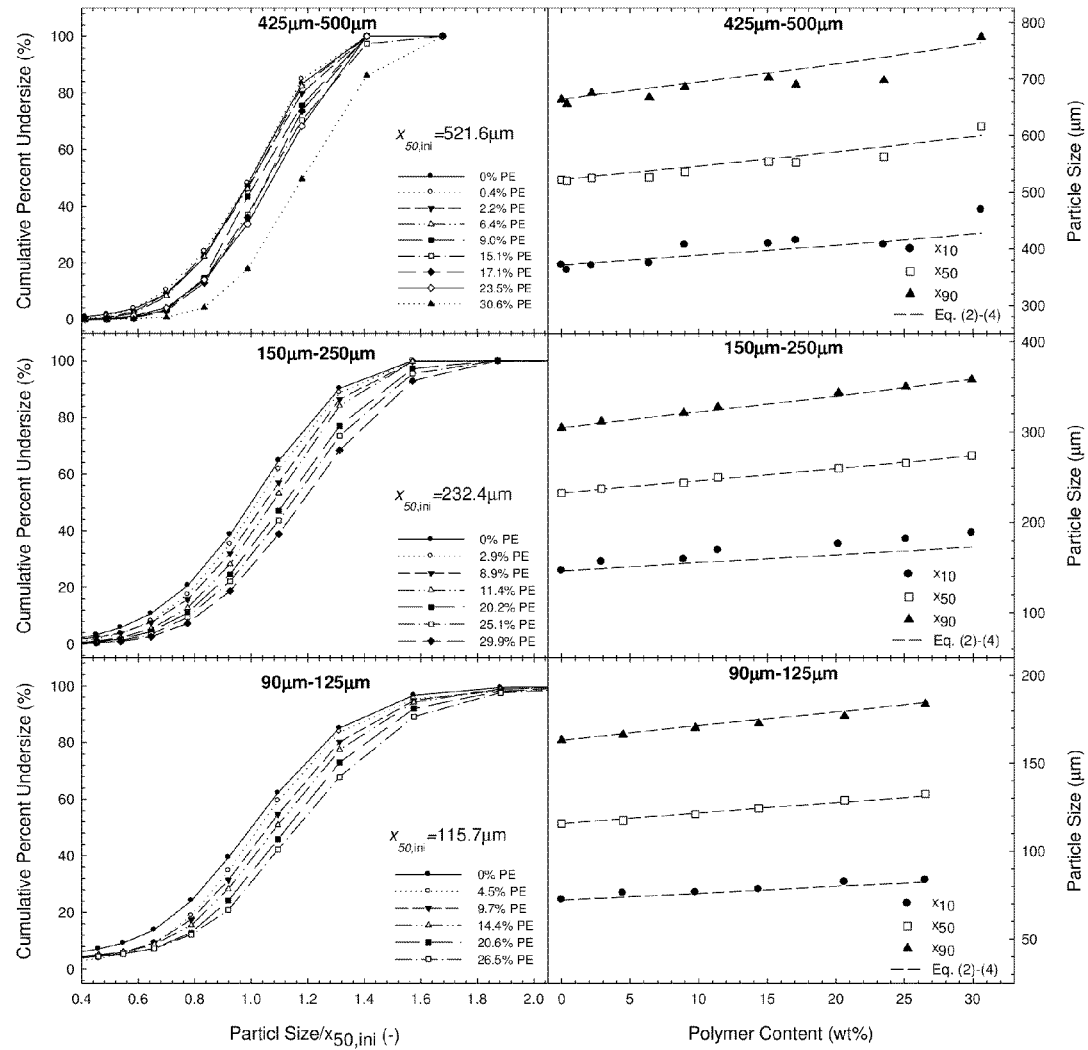
FIG. 31 shows cumulative percent undersize distribution for 425 μm-500 μm (top-left), 150 μm-250 μm (middle-left), and 90 μm-125 μm (bottom-left) processed with various PE wax loadings at condition listed in Table 9. Corresponding size statistics, $x_{10}$, $x_{50}$, $x_{90}$ (right) and theoretical size increase (right) calculated from Equations (2)-(4) is shown by dashed lines.
Figure 32:
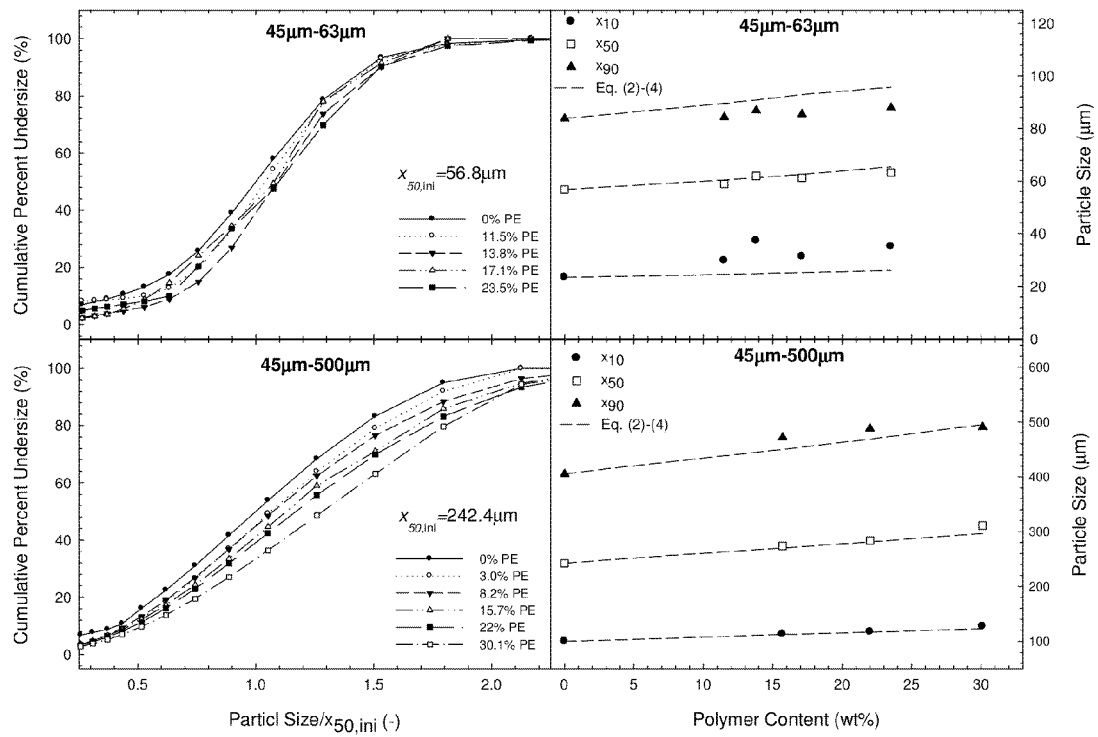
FIG. 32 shows cumulative percent undersize distribution for 45 μm-63 μm (top-left) and 45 μm-500 μm (bottom-left) processed with various PE wax loadings at conditions listed in Table 9. Corresponding size statistics, $x_{10}$, $x_{50}$, $x_{90}$ (right) and theoretical size increase (right) calculated from Equations (2)-(4) is shown by dashed lines.

The cumulative mass fraction particle size distribution and corresponding statistics ($x_{10}$, $x_{50}$, and $x_{90}$) for various sizes of ascorbic acid coated with 0-30 wt. % are shown in FIGS. 31-32. The size distributions determined by laser diffraction show no obvious feature of breakage or agglomeration of particles. Additionally the $x_{10}$, $x_{50}$, and $x_{90}$ all rise linearly with polymer content also confirming that there is no agglomeration or sticking of fine particles to coarser ones. There is a bit of scatter in the size measurements for 425 μm-500 μm ascorbic acid because the particle size was approaching the upper detection limit of the particle size analyzer.

In order to estimate the polymer thickness, which is necessary from a design perspective, the idea of surface coverage was used. The number of coating particles needed to cover the surface of a host with a monolayer can be estimated from simple geometry. Since, the cross-sectional area of the coating particles must occupy the surface area of the host layered with coating particles, the number of PE wax particles needed form a monolayer of ascorbic acid is given by Eq. (2), $$N = \frac{24(l_{AA} + d_{PE})^2}{\pi d_{PE}^2} \quad (2)$$

where is the side length of a cubical ascorbic acid particle, and $d_{PE}$ is the diameter of PE wax which is assumed to be spherical. Since N gives the number of particles to coat a monolayer (i.e. one surface coverage), the number of layers or surface coverage multiples, SC that may theoretically be formed by a given mass of PE wax and ascorbic acid is given by Eq. (3), $$SC = \left(\frac{\text{wt \%}_{PE}}{\text{wt \%}_{AA}}\right)\left(\frac{l_{AA}^2 \rho_{AA}}{N\frac{\pi}{6} d_{PE}^3 \rho_{PE}}\right) \quad (3)$$

Where $\rho_{AA}$ and $\rho_{PE}$ is the particle density of ascorbic acid and PE wax respectively. Then it proceeds that the number of layers of PE wax adhered to ascorbic acid (i.e. SC) corresponds to a coating layer thickness, $t_{coating}$ after the deformation process given by Eq. (4), $$t_{coating} = (SC)(d_{PE} f_{deform}) \quad (4)$$

where $f_{deform}$ is a deformation factor and was included to account for the deformation/compression of the polymer layers induced by impactions. Since the deformation factor is the only unknown in this set of equations (all others are directly measurable), it was used as a "fitting parameter". In estimating the polymer thickness, it was also assumed that PE wax was mono-dispersed in size with a diameter equal to its median size. Additionally, for SC>1, it was assumed that the coating material follows hexagonal close packing as one layer of polymer stacks upon another. Additionally, $l_{AA}$ is updated accordingly with each separate coating applied to the surface to account for the increase in particle surface area due to the coating particles.

Equations (2)-(4) were used to estimate the particle diameter for the $x_{10}$, $x_{50}$, and $x_{90}$ for various polymer contents and host particle sizes and are shown in FIGS. 31-32. The theoretical polymer thickness predicts the increase in particle diameter very well for all sizes. Excluding the 45 μm-63 μm ascorbic acid, the experimentally measured values of the $x_{10}$, $x_{50}$, and $x_{90}$ match the theoretical values concluding that there is equal sharing of the PE wax on a per mass basis meaning that larger particles are not preferentially coated over finer particles or vice versa though none of the size distributions are particularly wide. For 45 μm-63 μm ascorbic acid, the $x_{10}$ increased greater than what was expected while the $x_{90}$ increased less than what was expected meaning that the finest particles were preferentially coated with PE wax to some degree.

As previously stated, a deformation factor was needed to accurately estimate the coating thickness. Interestingly, the deformation factor is quite similar for 45 μm-63 μm, 90 μm-125 μm, 150 μm-250 μm, and 425 μm-500 μm ascorbic acid which respectively had values of 0.70, 0.60, 0.72, and 0.60, all showed significant deformation/compression. Because there are major differences in processing conditions and particle size, this consistency in the deformation factor may be a characteristic of the polymer and may be related to its deformability (i.e. Young's modulus). Conversely, the 45 μm-500 μm ascorbic acid had a deformation factor of 0.9.

Figures 33A, 33B, 33C, 33D:
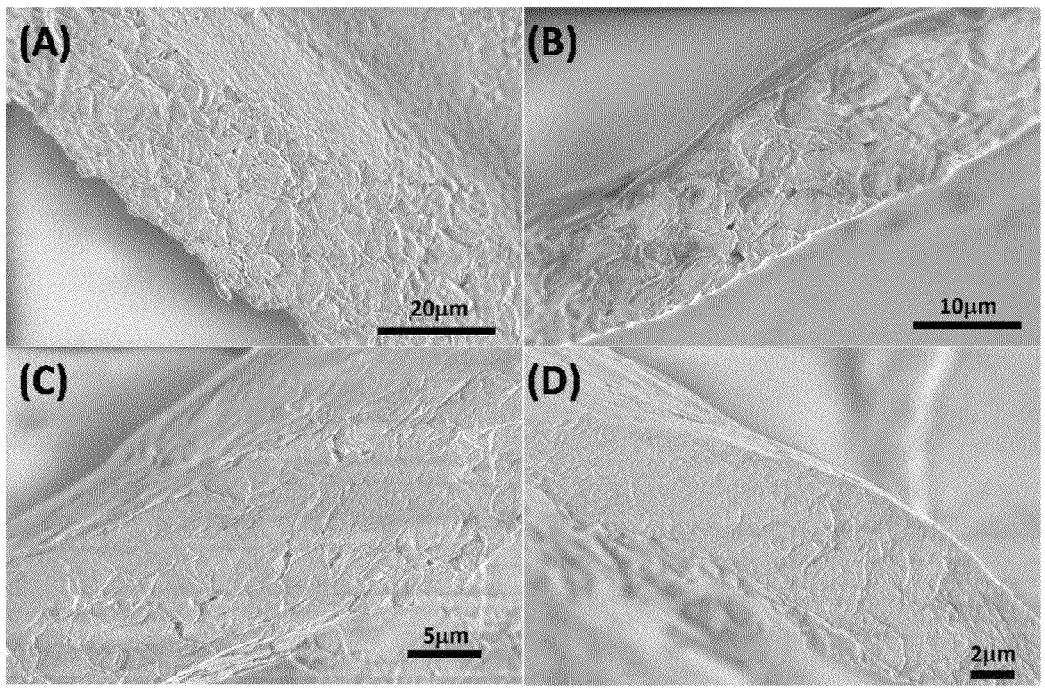
FIGS. 33A-33D show SEM images of polymer shell cross section from, (a) 425 μm-500 μm ascorbic acid coated with 23.5 wt % PE (SC~7.4), (b) 425 μm-500 μm ascorbic acid coated with 15.1 wt % PE (SC~4.7), (c) 250 μm-500 μm ascorbic acid coated with 29.9 wt % PE (SC~4.4), (d) 90 μm-125 μm ascorbic acid coated with 26.5 wt % PE (SC~2.0).

In this surface coverage based analysis of coating thickness, it may be questionable whether PE wax will actually form multiple layers before deforming into a continuous film. For this reason, a sample of 425 μm-500 μm ascorbic acid coated with 23.5 wt % PE wax was dissolved in water leaving behind only the polymer shell which was bisected and imaged by SEM as shown FIG. 33A. Based on the median size, $x_{50}$ the SC is expected to be 7.5 and the actual thickness is expected to be 29.2 μm based on the deformation factor. FIG. 33A shows excellent agreement, where a best estimate for the SC is indeed about 7 and a thickness is about 30 μm. This result gives great credence to the analysis used to estimate surface coverage and polymer thickness. Furthermore, from FIG. 33A, it seems as though only the outer surface of the PE wax is deformed into a continuous layer whereas subsequent layers remain mostly discrete but compressed forming a porous inner coating.

Figure 34:
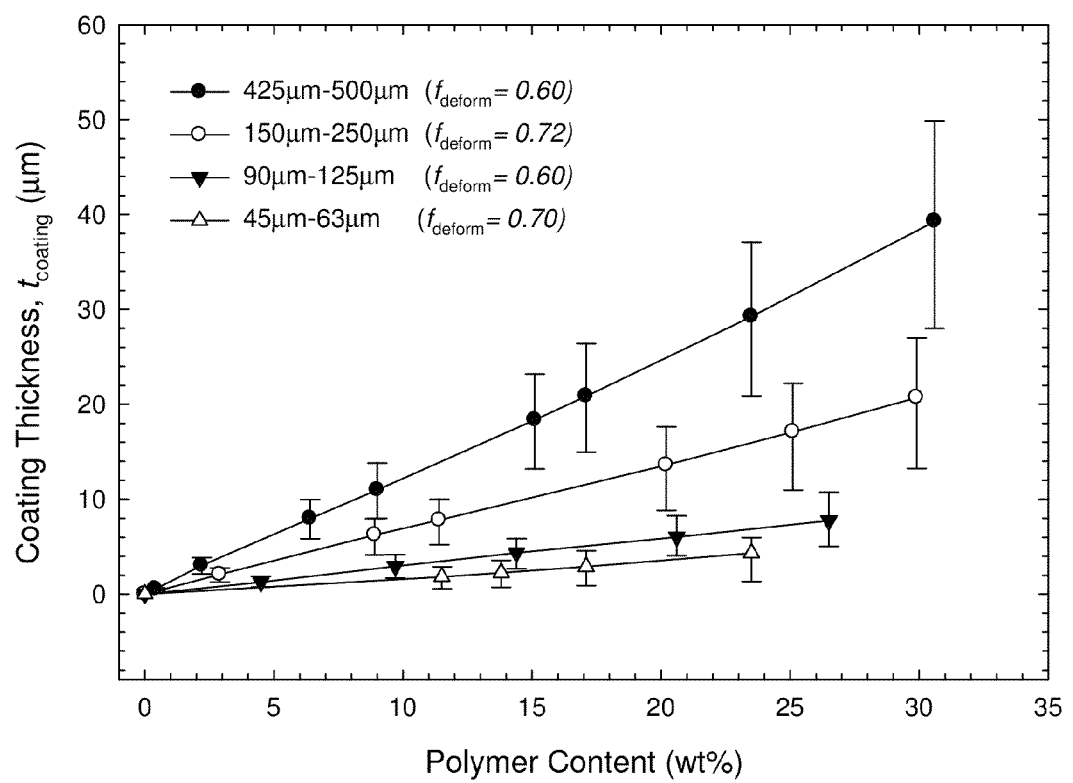
FIG. 34 shows the coating thickness for various sizes of ascorbic acid coated with various amounts of PE wax processed by conditions listed in Table 9. Coating thickness is derived from Eqs. (2)-(4) and the deformation factors. Points correspond to the coating thickness for the $x_{50}$, top bars correspond to the $x_{90}$, and bottom bars correspond to the $x_{10}$.

Since the theoretical determination of the coating thickness predicted particle size measurements very well, they were re-plotted in FIG. 34 to express the relationship of coating thickness to polymer content and host particle size. FIG. 34 clearly shows that a wide range of coating thickness (0-50 μm) can be achieved by dry-polymer-coating. Additionally, host particle size poses a significant limitation on coating thickness. 45 μm-63 μm ascorbic acid, due to its high surface area, requires a large amount of polymer (~25 wt. %) to achieve coating thicknesses of about 5 μm. On the other hand, 425 μm-500 μm ascorbic acid requires only ~5 wt. % to achieve the same thickness. Still, dry-polymer-coating was shown to coat particles from 56.8 μm-521.6 μm without agglomeration or breakage. Furthermore, the coating thickness was able to be accurately predicted and may serve as a useful tool in microparticle design for example in control release application as discussed in the next example.

Example 23

Figure 35:
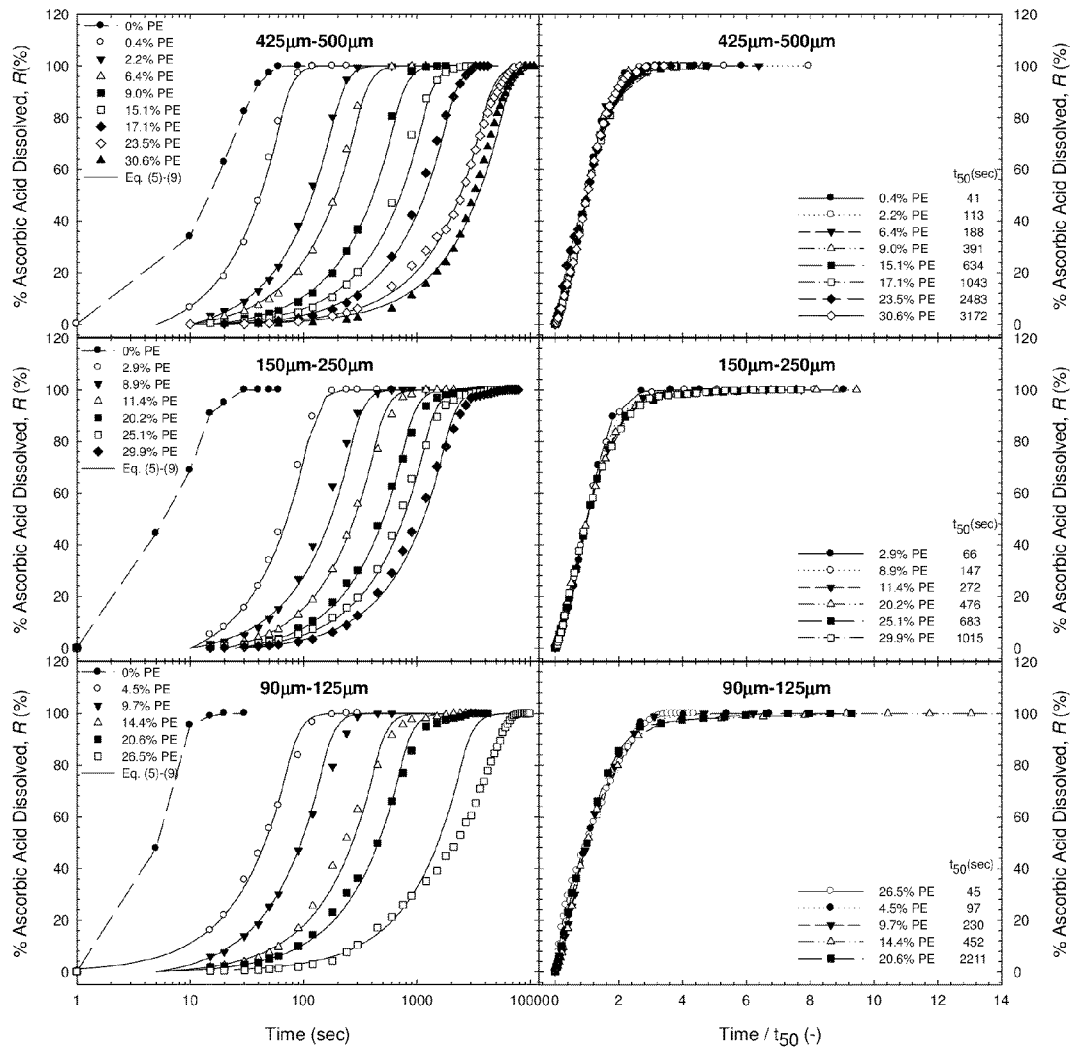
FIG. 35 shows release profiles of 425 μm-500 μm (top-left), 150 μm-250 μm (middle-left), and 90 μm-125 μm (bottom-left) processed with various PE wax loadings at conditions listed in Table 9. Experimental data given by points and a dissolution model. Release profiles normalized by $t_{50}$ showing self-similarity are given on the right.
Figure 36:
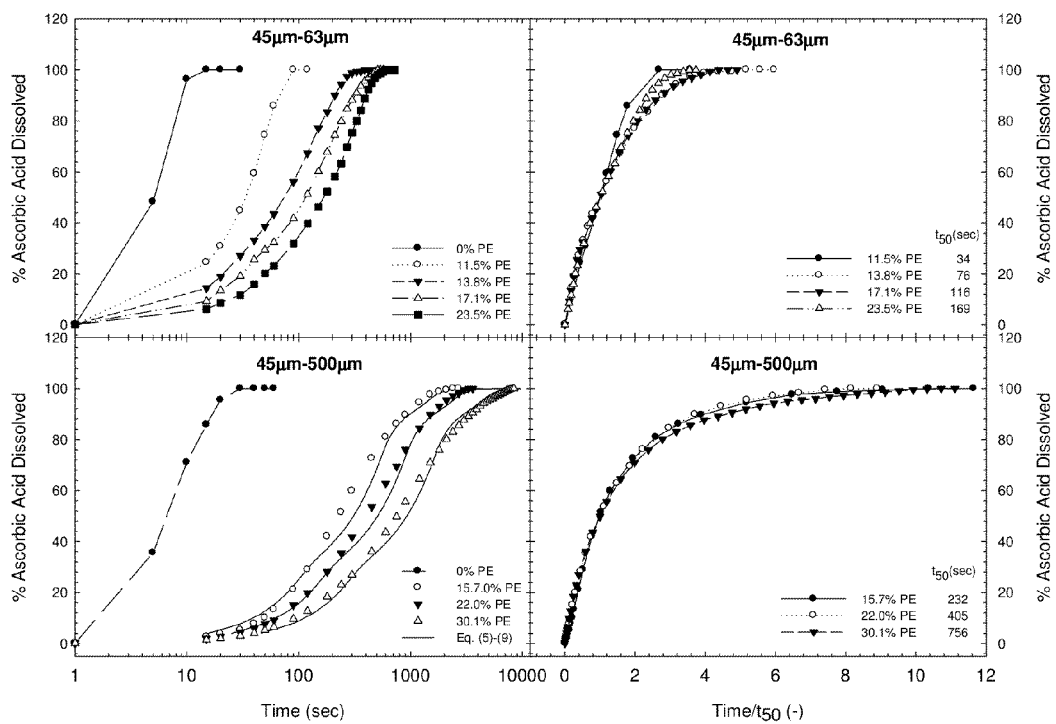
FIG. 36 shows release profiles of 45 μm-63 μm (top-left) and 45 μm-500 μm (bottom-left) processed with various PE wax loadings at conditions listed in Table 9. Experimental data given by points and a dissolution model given by solid lines. Release profiles normalized by $t_{50}$ showing self-similarity are given on the right.

In order to assess the controlled release potential of dry-polymer-coating, the ascorbic acid that was processed for particle size characterization in Example 22 was also subjected to dissolution testing. FIGS. 35-36 show the release profiles pertaining to ascorbic acid of various sizes and polymer contents (i.e. coating thicknesses). Ascorbic acid is highly water soluble and as shown in these figures a substantial reduction in dissolution rate is observed after coating with PE wax. 425 μm-500 μm ascorbic acid dissolves in less than 60 seconds, but when coated with 30 wt. % PE, complete dissolution takes 2.5 hours which gives a dissolution rate over two orders of magnitude slower. Similarly, 150 μm-250 μm ascorbic acid dissolves in less than 60 seconds, but when coated with 30 wt. % PE takes more than 1.5 hours to fully dissolve. 90 μm-125 μm dissolves in less than 20 seconds, but when coated with 27 wt. % PE takes more than 2 hours to fully dissolve. 45 μm-63 μm ascorbic acid, due to its thin coating, was dissolved in 10 minutes when coated with 24 wt. % PE compared to 10 seconds when left uncoated. These results are quite remarkable considering that the dissolution pertains to the primary microparticles and not to granules, pellets, or tablets. Furthermore, a reduction in dissolution rate is typically observed after lengthy curing steps as in plasticizer-dry-polymer-coating, but in this process it can be avoided while achieving a large reduction in dissolution rate.

To examine the dissolution mechanism, the time it takes for 50% of the sample to dissolve, $t_{50}$ was determined Normalizing the dissolution time by the $t_{50}$ for each sample showed self-similar behavior between samples as seen in FIGS. 35-36. The self-similarity shows that despite the amount or thickness of polymer, the host dissolves by the same mechanism with only a difference in the time scale. In this case, the linear profile of % ascorbic acid dissolved vs. time points towards a zero-order diffusion mechanism. This conclusion is valid for 90 μm-125 μm, 150 μm-250 μm, and 425 μm-500 μm ascorbic acid. The 45 μm-63 μm and 45 μm-500 μm ascorbic acid still show self-similar dissolution behavior, but deviate somewhat from zero-order release and show a dissolution rate slower than what would be expected.

In this section, we have shown that the release rate of highly water soluble ascorbic acid was significantly reduced by dry-polymer-coating without plasticizers, solvents, or additional heat treatments. Zero-order release, a type of mechanism beneficial for extended release pharmaceutical formulations, was achieved for 425 μm-500 μm, 150 μm-250 μm, and 90 μm-125 μm ascorbic acid. Surface coverage was shown to have a large effect on the release rate/diffusivity. These results can reasonably be extended to other drugs including poorly water soluble drugs for prolonged release formulations in a variety of dosage forms including strip films, oral dispersibles, tablets, and capsules.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

Example 24

Discrete Wax Versus Deformed Wax

Figure 37:
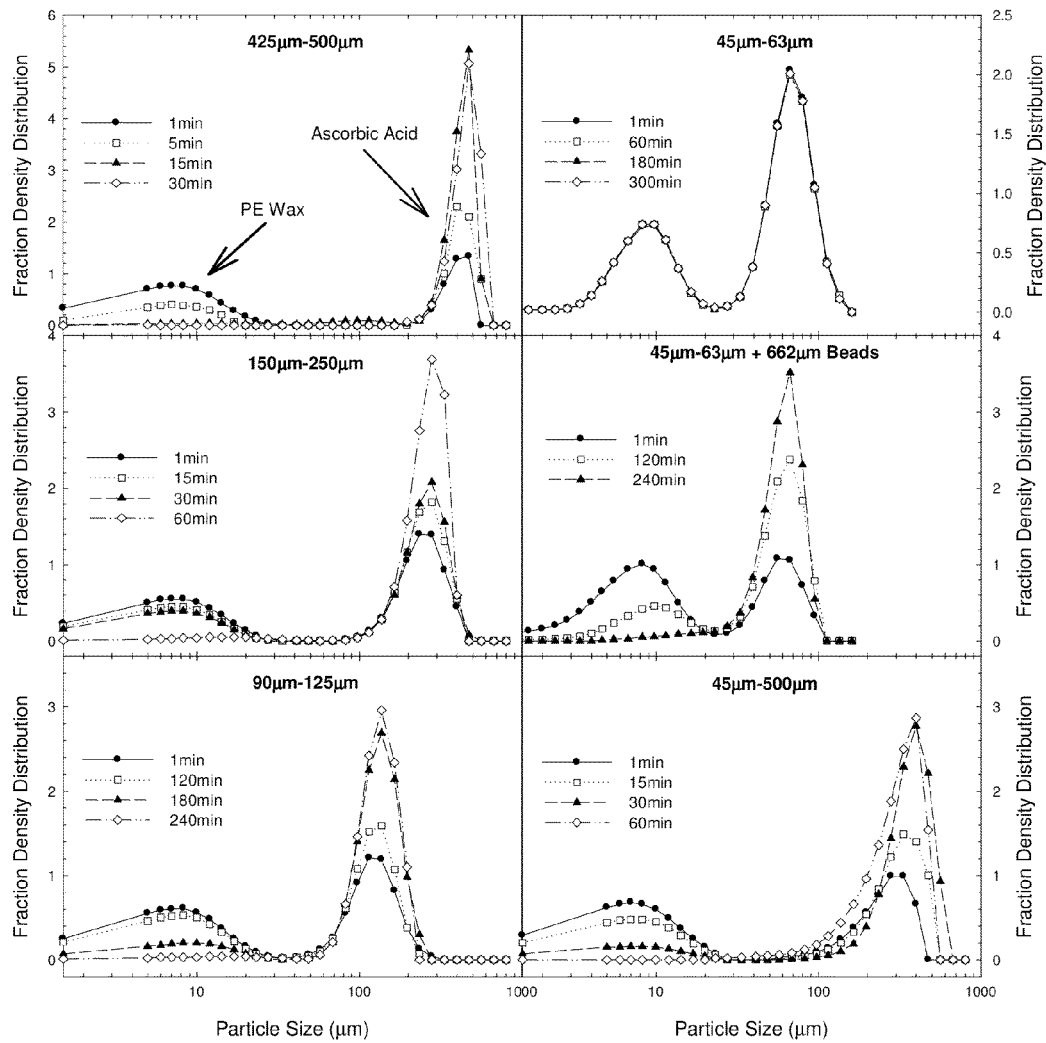
FIG. 37 shows the mass fraction density distribution for various sizes of ascorbic acid processed in a LabRAM at 100 g's with 25 wt % PE wax for various processing times. The peak at 6 μm corresponds to un-deformed PE wax removed from the surface of the ascorbic acid.
Figure 38:
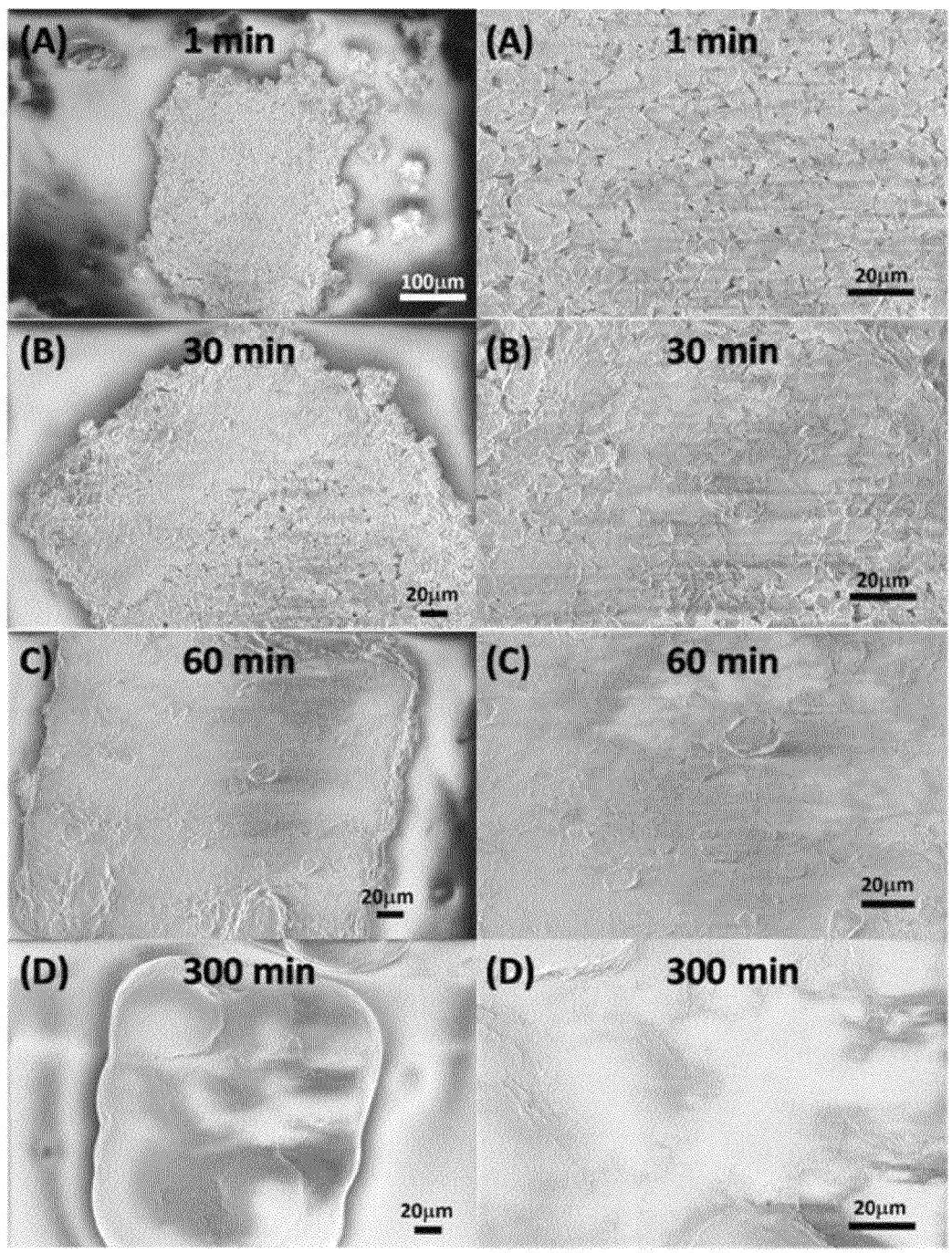
FIG. 38 shows SEM images of 90 μm-125 μm particle sizes of ascorbic acid processed in a LabRAM at 100 g's with 25 wt % PE wax at, (a) 1 minute, (b) 120 minutes, (c) 240 minutes, and (d) 300 minutes.
Figure 39:
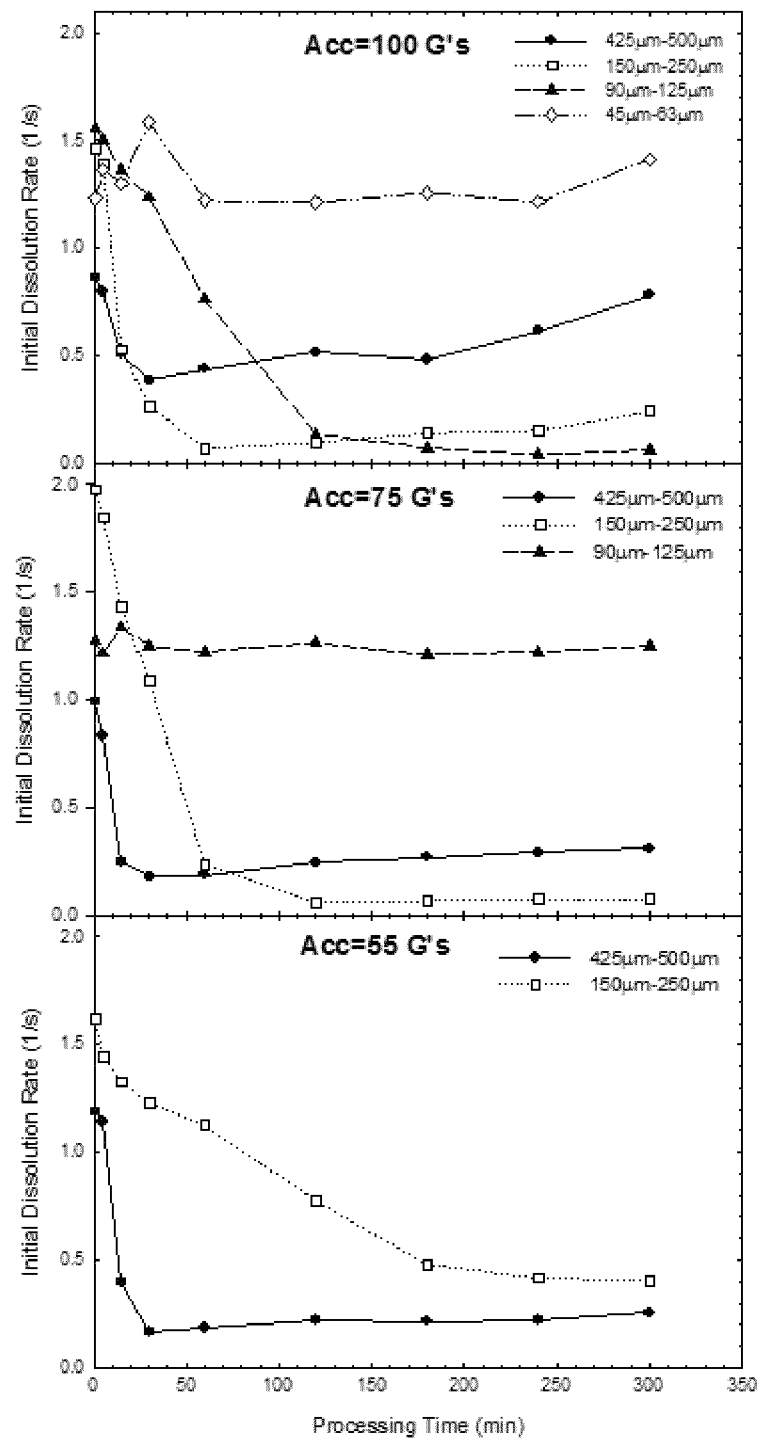
FIG. 39 shows initial dissolution rates for various sized particles of ascorbic acid processed in a LabRAM with 25 wt % PE wax from 1 minute-300 minutes at, 100 g's (top), 75 g's (middle), and 55 g's (bottom). A decrease in the dissolution rate corresponds to a transformation from a discrete to a continuous coating.

Particle size measurements were performed before and after processing in order to determine the thickness of the polymer layer after the dry-coating procedure and also to determine any effects of particle breakage or agglomeration. The Helos laser diffraction particle size analyzer used in this study was equipped with the Rodos powder dispersion unit. The powder dispersion unit used compressed air to disperse cohesive powders that otherwise would be measured as agglomerates instead of primary particles. Such measurements may be used to identify or illustrate the nature of coating based on the selected process intensity and processing time. If the coating is not well-spread and well-deformed, the wax particles may detach from the surface. It was observed that when PE wax remained as discrete particles rather than deformed layer on the surface of ascorbic acid, the dispersion unit could separate the two components. Thus, after measurement, a distinct contribution from the PE wax and the ascorbic acid could be observed in the particle size distribution. The particle size distributions for various samples are shown in FIG. 37. For all samples processed at 1 minute, a large contribution in the density distribution can be seen in the 1-20 μm range, which corresponds to the size of the PE wax. Even for the 5 minute processing, there is substantial presence of the particles in the finer range, although as expected, less than at 1 minute processing time. Since PE wax exists as discrete particles at this time, as seen in SEM images, they can be pulled free of the surface of ascorbic acid and measured individually. At longer processing times when the discrete polymer layer is deformed, there is a smaller contribution from the peak corresponding to the PE wax. At even longer processing times when the discrete layer has been completely deformed into a continuous layer, the peak for PE wax is not observed. The processing times when no peak for PE wax is observed also correspond well with SEM images, for example, FIG. 38 and the minimum dissolution rates, for example, FIG. 39. As a result, such particle size measurements can also determine whether the polymer exists as discrete particles or a continuous layer due to deformation and can also be used to test the integrity of the coatings.

Example 25

Surface Area Measurement to Evaluate Quality of Coating

PE wax, 20 wt %, was coated onto ascorbic acid, $d_{50}$=405 micron, in LabRAM at 75G's and samples were taken at 5 minutes, 30 minutes, and 2 hours of processing time. At 5 minutes, the coating was observed to be discrete, nearly similar to SEM images shown in FIG. 38 section (a), and it had a surface area of 3.71 m²/g, using a surface area analyzer option of the Surface Energy Analyzer (New Inverse Gas Chromatography instrument, SEA, from Surface Measurement Systems, Ltd., UK). At 30 minutes, the coating is fully deformed and a much reduced surface area of 0.88 m²/g was measured. At 2 hours, existence of attrition was observed and the measured surface area increases, and was 1.21 m²/g. The increase in surface area is attributed to the presence of fines due to over-processing at overly intense mixing conditions. In was also observed that dissolution rate also increases at these prolonged processing time (see for example, FIG. 39; corroborated through surface area measurements. As a reference, the surface area of the 405 micron ascorbic acid by itself is expected to be much less, e.g., about 0.01 m²/g, whereas the surface area of unprocessed fine wax was measured to be over 30 m²/g. Thus, a physical mixture of these components in the same proportions would have surface area of about 6 m²/g, thereby confirming that the composite coated powder exhibiting a high surface area, indicates that the coating is not well-deformed and uniform. Likewise, lower surface area indicates a higher level of deformation. While this example is illustrative of the role of the surface area due to porous coating, such an approach can also provide an indication of coating, since for surface area as a clear decrease from fully discrete to fully continuous coating and then a rise due to some attrition.

The foregoing examples have been presented for the purpose of illustration and description only. The scope of the invention is to be determined from the claims appended hereto.

What is claimed is:

1. A process for preparing a particulate pharmaceutical formulation from core particles comprising an active pharmaceutical ingredient, comprising the step of:
   mixing the core particles, water soluble and/or water swellable coating material particles, and substantially water insoluble polymer particles, to produce the particulate pharmaceutical formulation comprising coated core particles; and
   subjecting the coated core particles to mechanical stress to deform a coating on the coated core particles into a substantially continuous or continuous film;
   wherein a volume averaged median particle size of the core particles is at least three times greater than a median particle size of both the water soluble and/or water swellable coating material particles and the substantially water insoluble polymer particles;
   less than 0.1% of the active pharmaceutical ingredient dissolves in a dissolution test indicative of taste-release in the mouth in 60 seconds; and
   at least 90% of an amount of the API that would have been released from uncoated core particles of a same composition and size in a United States Pharmacopeia dissolution test indicative of dissolution in the gastrointestinal tract is released within 30 minutes.

2. The process of claim 1, wherein the active pharmaceutical ingredient is completely released from the particulate pharmaceutical formulation in 30 minutes in the United States Pharmacopeia Dissolution Test.

3. The process of claim 1, wherein the volume averaged median particle size of the core particles is in a range of from 10 μm to 1000 μm.

4. The process of claim 3, wherein the volume averaged median particle size of the core particles is in a range of from 40 μm to 500 μm.

5. The process of claim 1, wherein the median particle size for the water soluble and/or water swellable material particles and the substantially water insoluble polymer particles is independently selected to be in a range of from 1 μm to 20 μm.

6. The process of claim 1, wherein the soluble and/or water swellable coating material particles are hydrophilic polymer particles comprising a polymer selected from the group consisting of hydroxypropylmethylcellulose, hydroxypropylcellulose, poly-(ethylene oxide), polymethacrylates, lactose and combinations thereof.

7. The process of claim 1, wherein the substantially water insoluble polymer particles comprise a polymer selected from the group consisting of polyethylene, polypropylene, polytetrafluoroethylene, carnauba wax, castor wax, polyamide wax, and combinations thereof.

8. The process of claim 1, wherein a ratio between the median particle size of the substantially water insoluble polymer particles and the median particle size of the water soluble and/or water swellable material particles is in a range of from 1:1.5 to 1:6.

9. The process of claim 1, wherein the water soluble and/or water swellable material particles comprise from 0.1 wt % to 25 wt. % of the total weight of the core particles, the substantially water insoluble particles and water soluble and/or water swellable material particles in the mixing step.

10. The process of claim 9, wherein the water soluble and/or water swellable material particles comprise from 0.5 wt. % to 20 wt. % of the total weight of the core particles, the substantially water insoluble particles and water soluble and/or water swellable material particles in the mixing step.

11. The process of claim 1, wherein the substantially water insoluble polymer particles comprise up to 50 wt. % of the total weight of the core particles, the substantially water insoluble particles and water soluble and/or water swellable material particles in the mixing step.

12. The process of claim 1, wherein the substantially water insoluble polymer particles comprise from 5 wt % to 25 wt % of the total weight of the core particles, the substantially water insoluble particles and water soluble and/or water swellable material particles in the mixing step.

13. The process of claim 1, wherein the particle number ratio between the water soluble and/or water swellable material particles and the substantially water insoluble polymer particles of the mixing step is in a range of from 1:10 to 1:100.

14. The process of claim 1, wherein the particle number ratio between the water soluble and/or water swellable material particles and the substantially water insoluble polymer particles of the mixing step is in a range of from 1:20 to 1:80.

15. The process of claim 1, further comprising a step of dry coating the water soluble and/or water swellable material particles with a hydrophobic silica having a median particle size not greater than 100 nm, prior to the mixing step.

16. The process of claim 15, wherein the hydrophobic silica has a median particle size not greater than 20 nm.

17. The process of claim 1, wherein the mixing step comprises steps of:
   1) preblending the water soluble and/or water swellable coating material particles and substantially water insoluble polymer particles;
   2) mixing the pre-blended water soluble and/or water swellable coating material particles and substantially water insoluble polymer particles with core particles to produce the coated core particles.

18. The process of claim 1, wherein the water soluble and/or water swellable material particles are added stepwise to the core particles and substantially water insoluble polymer particles during the mixing step.

19. The process of claim 1, wherein the substantially water insoluble polymer particles are added stepwise the core particles and water soluble and/or swellable material particles during the mixing step.

20. The process of claim 1, wherein media particles are present during the mixing step and the media particles have a volume averaged median particle size that is separable by sieving from the coated core particles.

21. The process of claim 20, wherein the media particles have a median particle size in a range of from 10 μm to 1000 μm.

22. The process of claim 20, wherein the media particles have a median particle size in a range of from 50 μm to 500 μm.

23. The process of claim 1, wherein the core particles comprise a mixture of core particles, and wherein at least one fraction of coated core particles are separable by sieving from at least another fraction of coated core particles.

24. The process of claim 20, wherein the particle number ratio between the core particles and the media particles in the mixing step is in a range of from 1:30 to 1:300.

25. The process of claim 20, wherein the particle number ratio between the core particles and the media particles in the ingredients of the mixing step is in a range of from 1:50 to 1:200.

26. The process of claim 1, further comprising a step of curing the coated core particles.

27. The process of claim 1, further comprising a step of dry coating the coated core particles with a hydrophobic silica having a median particle size in a range of from 20 nm to 500 nm.

28. The process of claim 27, wherein the hydrophobic silica has a median particle size in a range of from 50 nm to 200 nm.

29. The process of claim 1, wherein at least 95% of an amount of the API that would have been released from uncoated core particles of a same composition and size in a United States Pharmacopeia dissolution test indicative of dissolution in the gastrointestinal tract is released within 30 minutes.

30. The process of claim 1, wherein at least 99% of an amount of the API that would have been released from uncoated core particles of a same composition and size in a United States Pharmacopeia dissolution test indicative of dissolution in the gastrointestinal tract is released within 30 minutes.

31. The process of claim 1, wherein less than 1% of the API dissolves in a dissolution test indicative of taste-release in the mouth in 120 seconds.

32. The process of claim 1, wherein less than 0.5% of the API dissolves in a dissolution test indicative of taste-release in the mouth in 120 seconds.

33. The process of claim 1, wherein the mixing step and the step of subjecting the coated core particles to mechanical stress to deform a coating on the coated core particles into a substantially continuous or continuous film are carried out simultaneously.

34. The process of claim 33, wherein the mixing step and the step of subjecting the coated core particles to mechanical stress to deform a coating on the coated core particles into a substantially continuous or continuous film are carried out by vibration with an intensity number of 10-100.

35. The process of claim 33, wherein the mixing step and the step of subjecting the coated core particles to mechanical stress to deform a coating on the coated core particles into a substantially continuous or continuous film are carried out by acoustic mixing.

36. The process of claim 35, wherein the acoustic mixing has a vibration intensity number of 10-100 at a frequency of about 60 Hz.

37. The process of claim 1, wherein the step of subjecting the coated core particles to mechanical stress deforms the coating on the coated core particles into a continuous film.

* * * * *